(12) United States Patent
Cabral

(10) Patent No.: US 11,931,130 B2
(45) Date of Patent: Mar. 19, 2024

(54) METHOD AND SYSTEM FOR PROCESSING THERMAL VIDEO IMAGES

(71) Applicant: Paula Gebe Abreu Cabral, Campos dos Goytacazes (BR)

(72) Inventor: Paula Gebe Abreu Cabral, Campos dos Goytacazes (BR)

(*) Notice: Subject to any disclaimer, the term of this patent is extended or adjusted under 35 U.S.C. 154(b) by 491 days.

(21) Appl. No.: 17/275,976

(22) PCT Filed: Sep. 13, 2019

(86) PCT No.: PCT/BR2019/050398
§ 371 (c)(1),
(2) Date: Mar. 12, 2021

(87) PCT Pub. No.: WO2020/051669
PCT Pub. Date: Mar. 19, 2020

(65) Prior Publication Data
US 2022/0036600 A1 Feb. 3, 2022

(30) Foreign Application Priority Data
Sep. 14, 2018 (BR) .......................... 102018068627-5

(51) Int. Cl.
*A61B 5/01* (2006.01)
*A61B 5/00* (2006.01)
(Continued)

(52) U.S. Cl.
CPC ............ *A61B 5/015* (2013.01); *A61B 5/0075* (2013.01); *G06T 7/0012* (2013.01);
(Continued)

(58) Field of Classification Search
CPC ..... A61B 5/0075; A61B 5/0077; A61B 5/015; A61B 5/4312; A61B 5/7267; G01K 3/14;
(Continued)

(56) References Cited

U.S. PATENT DOCUMENTS

| 6,262,817 B1 | 7/2001 | Sato et al. | |
| 2007/0110290 A1* | 5/2007 | Chang | ........................ G06T 5/00 |
| | | | 382/280 |

(Continued)

OTHER PUBLICATIONS

Emilio Z. Barcelos, "A Combined Method for Segmentation and Registration for an Advanced and Progressive Evaluation of Thermal Images," Nov. 19, 2014, Sensors 2014, 14, 21950-21967; doi: 10.3390/s141121950, pp. 21950-21959.*

(Continued)

*Primary Examiner* — Omar S Ismail
(74) *Attorney, Agent, or Firm* — Laurence P. Colton; Smith Tempel Blaha LLC

(57) ABSTRACT

A method and system for processing thermal video images and thermal video images of patients, using a method of real-time demarcation of the macro aspect of the region of interest, generated by MIR and LIR electromagnetic wave emission and merging of the real image, with improvement of the image, also in real time, allowing for analysis of the micro aspect by means of NIR electromagnetic wave emission, for spectral identification of the sample by infrared vibrational spectroscopy. The method and system pertains to the fields of medicine, biomedicine, and electrical engineering.

9 Claims, 37 Drawing Sheets

(51) Int. Cl.
*G06T 7/00* (2017.01)
*G06T 11/00* (2006.01)
*G06V 10/143* (2022.01)
*H04N 5/33* (2023.01)

(52) U.S. Cl.
CPC .......... *G06T 11/001* (2013.01); *G06V 10/143* (2022.01); *H04N 5/33* (2013.01); *G06T 2200/24* (2013.01); *G06T 2207/10016* (2013.01); *G06T 2207/10048* (2013.01); *G06T 2207/20221* (2013.01)

(58) Field of Classification Search
CPC ............... G06T 11/001; G06T 2200/24; G06T 2207/10016; G06T 2207/10048; G06T 2207/20221; G06T 2207/30068; G06T 2207/30096; G06T 7/0012; G06V 10/143; G06V 2201/03
See application file for complete search history.

(56) References Cited

U.S. PATENT DOCUMENTS

| | | | | |
|---|---|---|---|---|
| 2007/0196007 | A1* | 8/2007 | Chen | A61B 6/00 |
| | | | | 382/131 |
| 2007/0213617 | A1* | 9/2007 | Berman | A61B 5/0091 |
| | | | | 600/473 |
| 2012/0330447 | A1* | 12/2012 | Gerlach | G01B 11/24 |
| | | | | 382/128 |
| 2015/0124102 | A1* | 5/2015 | Frost | H04N 5/33 |
| | | | | 348/165 |
| 2019/0306093 | A1* | 10/2019 | Schilling | G06F 16/2455 |

OTHER PUBLICATIONS

Huan-Wen Tzeng, "The Design of Isotherm Face Recognition Technique Based on Nostril Localization," Jul. 5, 2011, Proceedings 2011 International Conference on System Science and Engineering, pp. 1-4.*

M Kristo, "An Oberview of Thermal Face Recognition Methods," Jul. 2, 2018, 2018 41st International Convention on Information and Communication Technology, Electronics and Microelectronics (MIPRO), Opatija Croatia, pp. 1098-1100.*

Ming Yang, "Vital Sign Estimation from Passive Thermal Video," Aug. 5, 2008, 2008 IEEE Conference on Computer Vision and Pattern Recognition, pp. 1-4.*

U Snekhalatha, "Automated hand thermal image segmentation and feature extraction in the evaluation of rheumatoid arthritis," Apr. 30, 2015, Proceedings of the Institution of Mechanical Engineers, Part H: Journal of Engineering in Medicine, vol. 229, Issue 4, pp. 319-329.*

WIPO, International Search Report (on parent application), dated Nov. 8, 2019.

* cited by examiner

FIG. 34
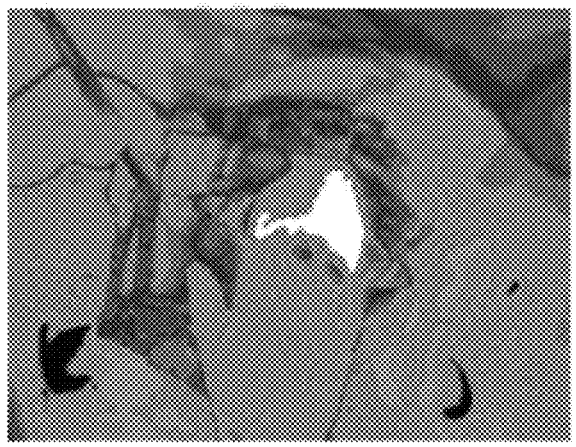 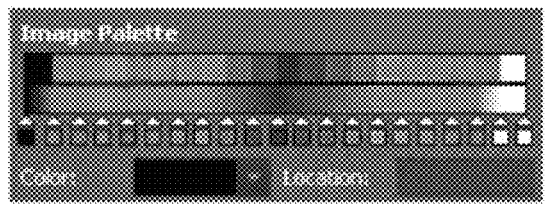
FIG. 35

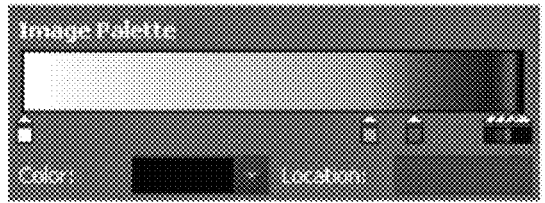
FIG. 40
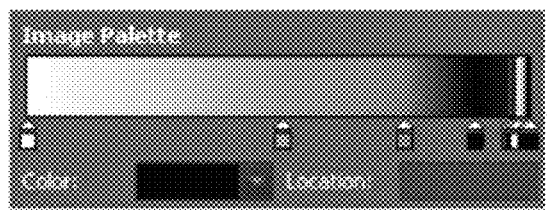
FIG. 41

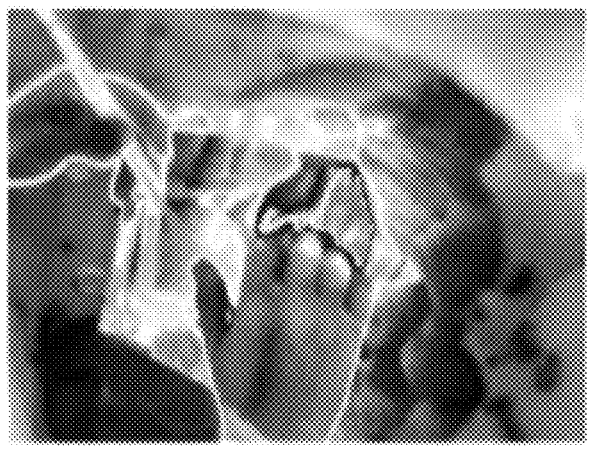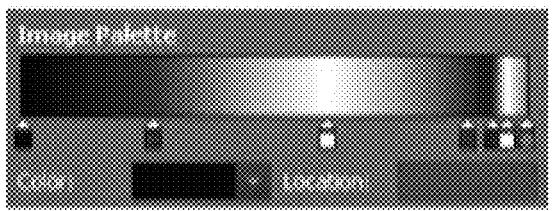
FIG. 42
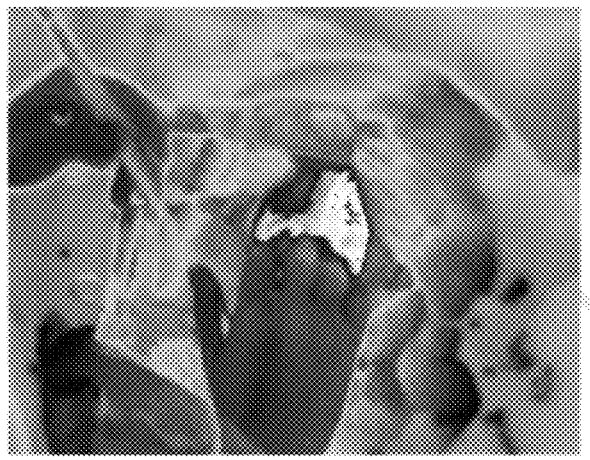
FIG. 43
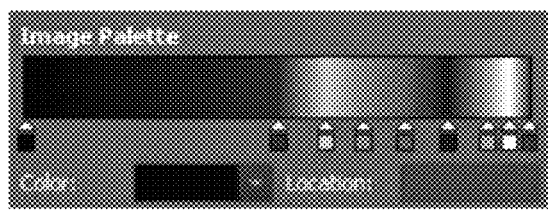
FIG. 44

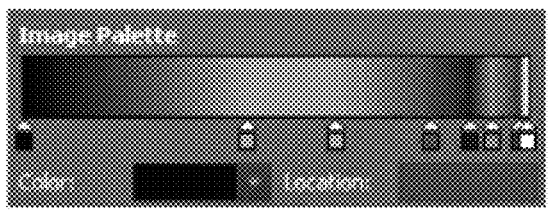
FIG. 45
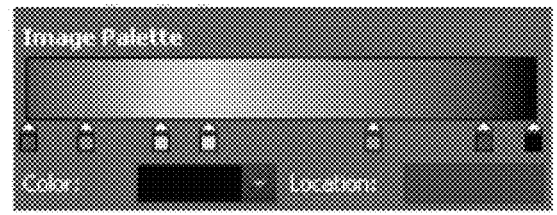
FIG. 46
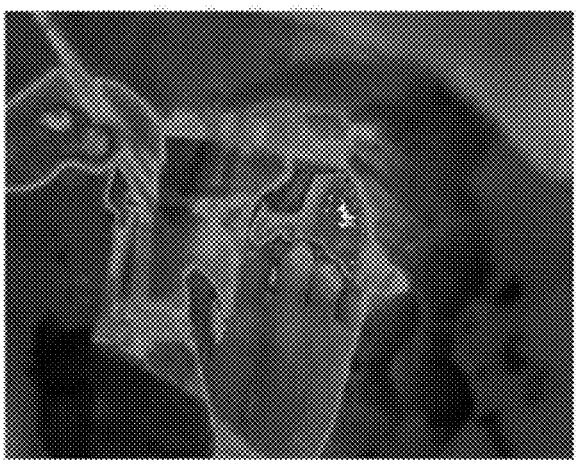
FIG. 47

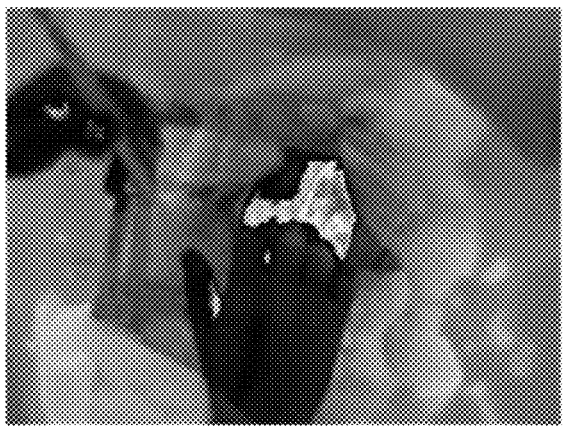 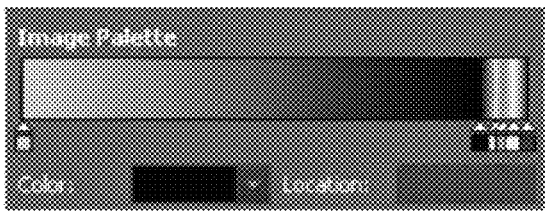
FIG. 48
 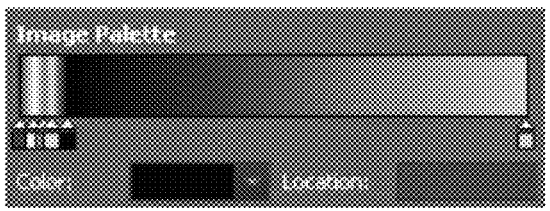
FIG. 49
 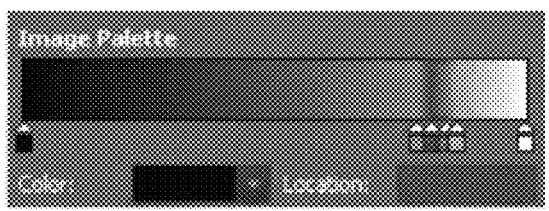
FIG. 50

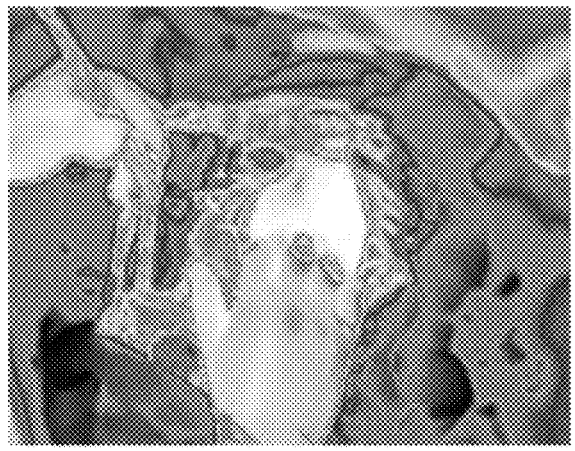
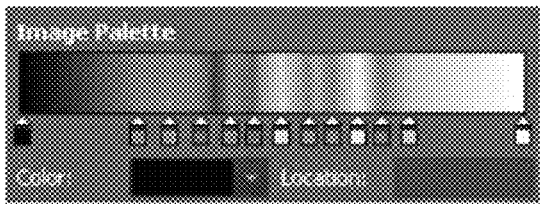
FIG. 51
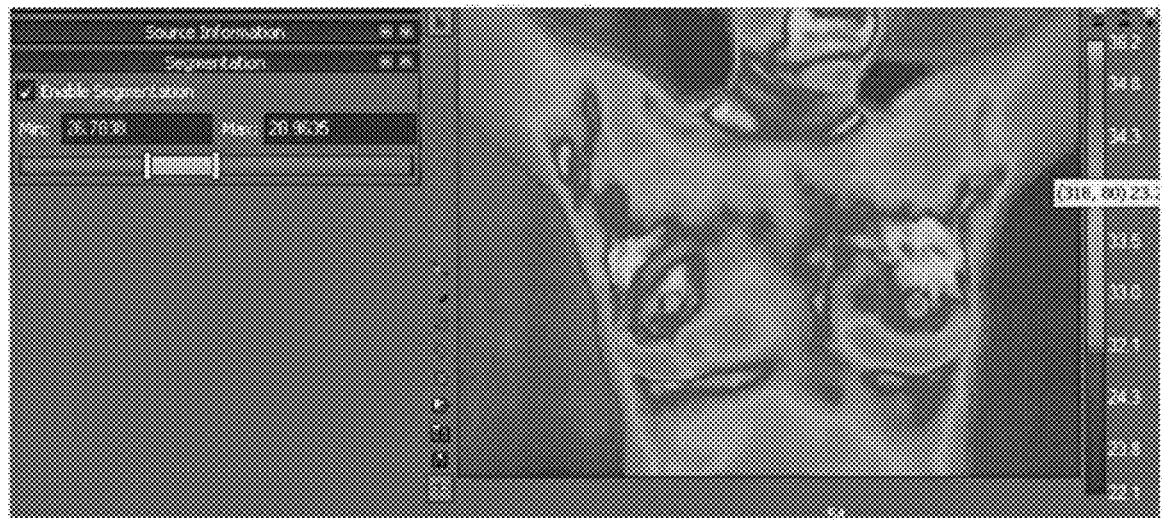
FIG. 52

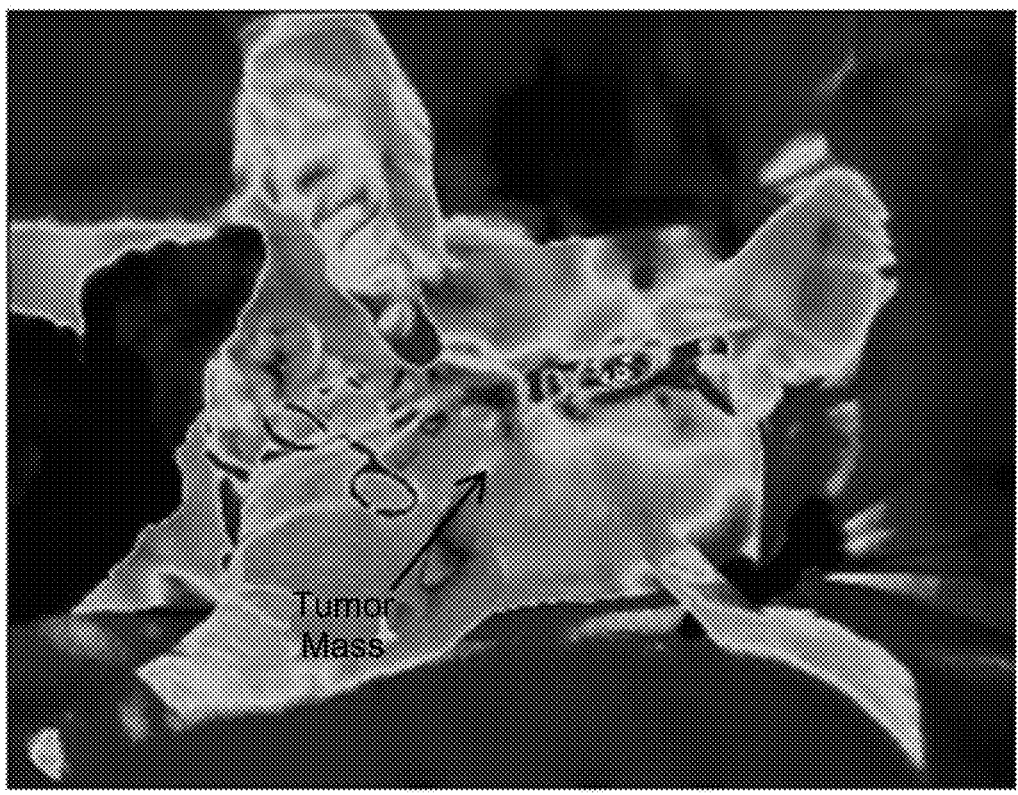
FIG. 65.A

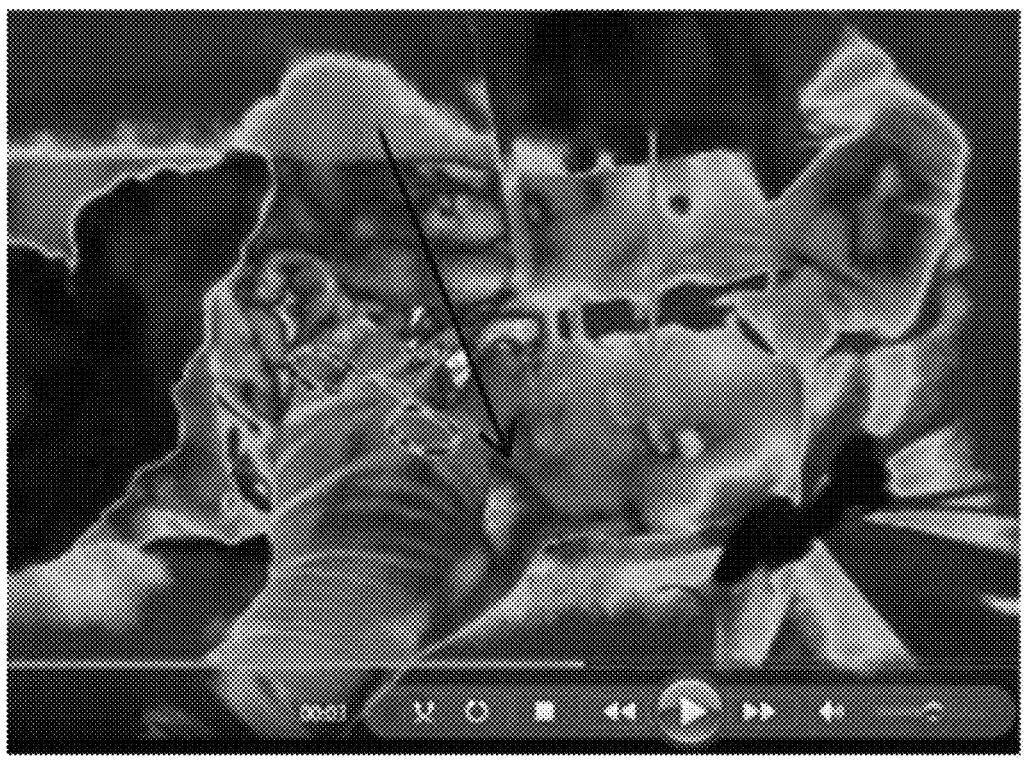
FIG. 65.B

METHOD AND SYSTEM FOR PROCESSING THERMAL VIDEO IMAGES

CROSS REFERENCE TO RELATED APPLICATIONS

This application is the US National Phase of and claims the benefit of and priority on International Application No. PCT/BR2019/050398 having a filing date of 13 Sep. 2019, which claims priority on and the benefit of Brazilian Patent Application No. 102018068627-5 having a filing date of 14 Sep. 2018.

BACKGROUND OF THE INVENTION

Technical Field

The present invention describes a method and system for processing thermometric video images of patients, which comprises a method for delimiting the macro aspect of the region of interest, generated by the emission of electromagnetic waves MIR and LIR and fusion of the real image, with image enhancement, enabling the analysis of the micro aspect by emitting NIR electromagnetic waves, for spectral identification of the sample by infrared vibrational spectroscopy. The present invention is pertained to the fields of medicine, biomedicine and electrical engineering.

Prior Art

By analyzing the electromagnetic spectrum, we realize that the most used imaging tests are at the extremes. The infrared portion of the spectrum has its main application in industrial inspection, automobile industry, steel industry, aeronautical industry, chemical industry, engineering, arts and electrical maintenance, being a reliable technique that helps to prevent interruptions in production processes, avoiding expenses and misfortunes (NOGUEIRA, 2010).

In the healthcare field, Nicholas A. Diakides was the main person, since he was manager of the infrared technology program at the US Army's night vision and electro-optic laboratory between 1962-1983, when he developed several applications for imaging by infrared, including "smart" image processing, computer aided detection (CAD), knowledge-based databases and telemedicine systems. With the collaboration of Diakides, the technique was regulated by the European Association of Thermology in 1972 (LAHIRI, 2012). In 2003, the FDA (Food and Drug Administration) regulated the test as "real-time digital thermometry". In Brazil, AMB (Brazilian Medical Association) regulated the "skin thermology" test, under number 39.01.007-4.

In cardiac surgery, the initial utility of thermometry video occurred in myocardial revascularization procedures, in which the method use ensured the viability of grafts and anastomoses in coronary surgeries (MOHR, 1989). It is also useful for patients suffering from angina, demonstrating that the thermal variation in the precordial region is greater than in normal patients, being confirmed by angiography (BRIOSCHI, 2002). In clinical cardiology, thermometry is used as an aid to the diagnosis of atherosclerotic cardiovascular disease, since it evidences a vascular dysfunction through the patient's skin, in specific areas, related to the level of occlusion by atheromas (THIRUVENGADAM, 2014).

It is noted that the used term in the industrial area is "Thermography for the technique and Thermogram for the exam", using static images. In the healthcare area, the regulated term is "Thermology for the technique and Thermometry for the exam" with dynamic images in real-time, where the thermometric image is a digital image that can be processed.

The difference in focus is what makes the thermometric image the object of our interest. The adaptation from industrial standard of "thermography" to the healthcare area (ARENA 2004; TAN, 2009; NOGUEIRA, 2010; RING 2013; QUESADA, 2016) has created the trend towards the use of static and multicolored images (rainbow) of industrial software (VADARSCA, 2014) underutilizing the technique, since it can give more information than it appears if we use a standard of image that takes into account the fact that the human being is a dynamic and homeothermic structure, being almost a black body. According to the theory of thermal radiation, the black body is considered as a hypothetical object that absorbs all incident radiation and radiates a continuous spectrum according to Planck's law. By integrating the Planck's law for all frequencies, we obtain Stefan Boltzman's law, which describes the total emission power of a black body (MODEST, 2013). Our skin is almost a black body with a radiation rate of 97 to 99%, with reflection from 1 to 3% (LAHIRI, 2012).

In 1987, Gautherie conducted a prospective study on more than 25,000 women, both asymptomatic (59%) and symptomatic (41%), for four years, with the aim of investigating the thermal and vascular disorders associated with the early stages of breast malignancy. All patients underwent a thermographic examination under standardized conditions, mammographies, physical test, and when indicated, complementary radiographic, ultrassonographic and cytological tests. From 294 in situ, microinvasive and non-palpable diagnosed cancers, 60-70% of them generated significant thermal anomalies that, in most cases, consisted of distorted thermovascular patterns. Two hundred and four (21.3%) of the 958 patients had an abnormal thermogram on their first visit, however, with no evidence on physical examination or mammography, they developed cancer in the following three years.

In 1996, Gamagami wrote in his Mammography Atlas that pre-neoplastic angiogenic changes can be observed in asymptomatic patients years before the clinical or mammographic manifestations of breast cancer. These findings in the past were interpreted as false positives and years later the palpable tumor itself developed in the same breast. In another study of women with thermal abnormalities at the initial examination, and followed for 2 to 10 years, 33% of these women developed breast cancer (FEIG, 1999).

Advances in imaging technologies have resulted in enhanced images, but each image modality has its own practical limitations, imposed by the nature of organ and tissue structures. These limitations reinforce the need to explore new technologies and explore the possibility of using multiple modalities of image (JAMES, 2014). According to Balan (2005), the characteristics most extracted from the images and used to generate the vectors are: color, texture and shape.

Color representation includes from the traditional RGB (red, green and blue) in an orthogonal Cartesian space, which maps the physical characteristics of the object, reflecting more precisely the color model for human perception in terms of hue, saturation and intensity (PHAM, 2000). Texture and shape can more accurately discriminate and separate the image, since objects (organs, tissues and anomalies) have, in most cases, specific shapes and textures that can be used to delimit them, and can be recognized and differentiated by human look through characteristics of smoothness, roughness and regularity (TUCERYAN, 1993).

Segmentation decomposes an image into homogeneous regions and this task can be achieved by identifying the boundaries between the regions of interest (ROI). In the view of Santos (2006), the regions of an image segmentation must be uniform and homogeneous in relation to some characteristics, such as gray tone or texture, while the adjacent regions must have significantly different values in relation to the characteristic in which they are uniforms. The segmentation limit must be simple, not tattered, and spatially precise (HARALICK, 1985).

A universal algorithm for image segmentation, certainly, does not exist and, on the contrary, most techniques are adapted for certain applications and can work only under certain hypotheses that are prone to segmentation errors if the objects depicted in the color images are affected by highlights, shading and shadows. The only way to overcome this disadvantage is analyzing how the light interacts with colored materials and introducing models of this physical interaction in the segmentation algorithms, accounting for the reaction properties with colored matter (PHAM, 2000).

The state of the art lacks of a system for processing thermometric video images of patients, which is able to locate the region of interest, record occurrences that although not visible—with the naked eye—are present, detect numerous anomalies in different types of images, in addition to being able to compare different images for use the most efficient one according to the operator's need. It also lacks of a system for identifying a region of interest, not visible or palpable, for spectral analysis of the sample.

Thus, from the researched literature, no documents were found anticipating or suggesting the teachings of the present invention, so that the solution proposed here has novelty and inventive activity in view of the state of the art.

BRIEF SUMMARY OF THE INVENTION

Therefore, the present invention solves the problems of the state of the art from a system for processing thermometric video images of patients capable of detecting anomalies by means of a video thermogram, using electromagnetic waves with different lengths within the infrared spectrum and an adjustment of the color palette of the obtained images.

In a first object, the present invention presents a method for processing thermometric video images of patients comprised of the steps of:
 a. delimitation of the region of interest and registration of anomalies not visible to the naked eye, through the emission of electromagnetic waves MIR and LIR;
 b. thermometry video of the region of interest through the emission of electromagnetic waves MIR and LIR;
 c. identification of anomalies not visible to the naked eye for spectral analysis of the sample by the emission of NIR electromagnetic waves;
 d. resolution setting of the generated video thermogram.

In a second object, the present invention shows a system for processing thermometric video images of patients comprising:
 a. means of acquiring the video thermogram;
 b. means of handling the video thermogram.

These and other objects of the invention will be immediately valued by those skilled in the art and will be described in detail below.

BRIEF DESCRIPTION OF THE DRAWINGS

In order to better define and clarify the content of this patent application, the following figures are presented.

Presentation of the CURRENT STANDARD OF THERMOGRAPHIC IMAGE Adapted from Industrial Standard

Demonstration of ENHANCEMENT OF THE THERMOMETRIC VIDEO IMAGE Proposed

Figure 9:
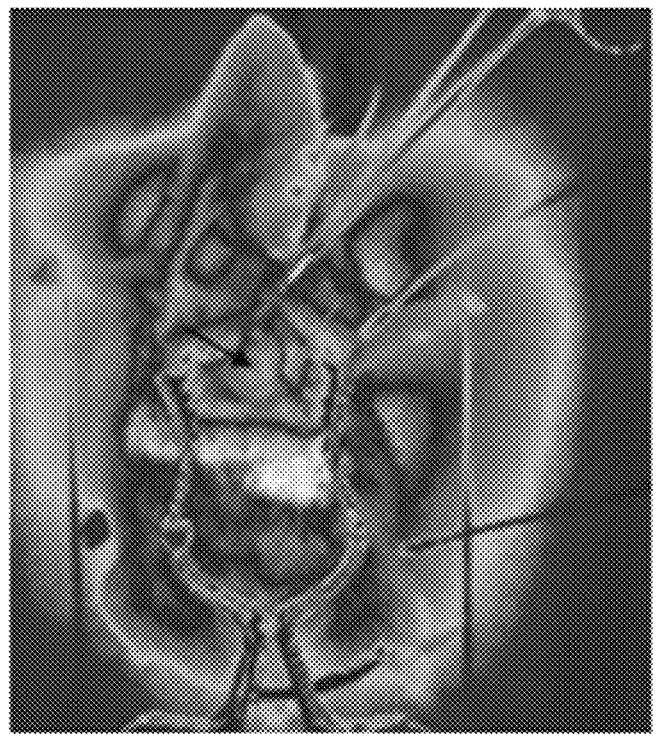
Figure 10:
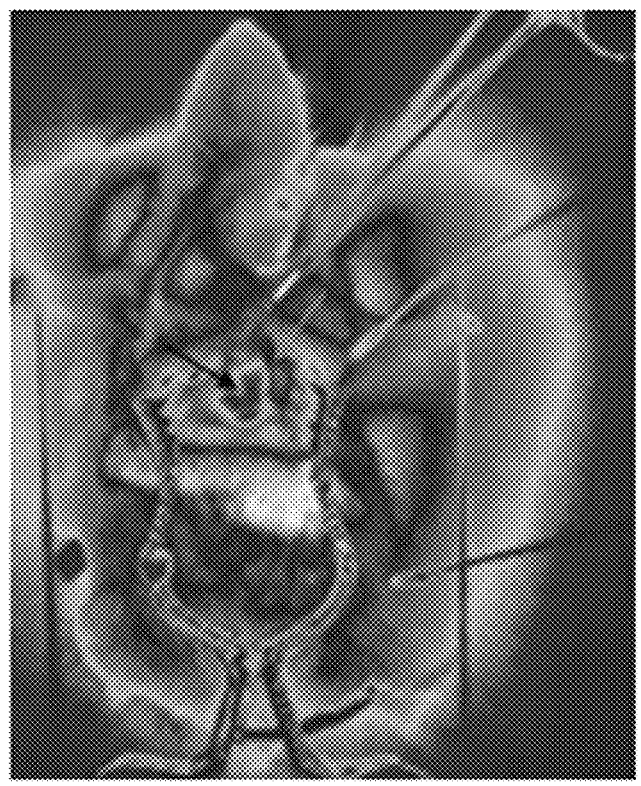

FIGS. 9 and 10 show, through the color palette, the outline that occurs of lung (black arrow) and heart (yellow arrow) of a rat, which lost heat to the environment (22±2° C.) during the experiment in order to decrease its temperature.

Figure 11:
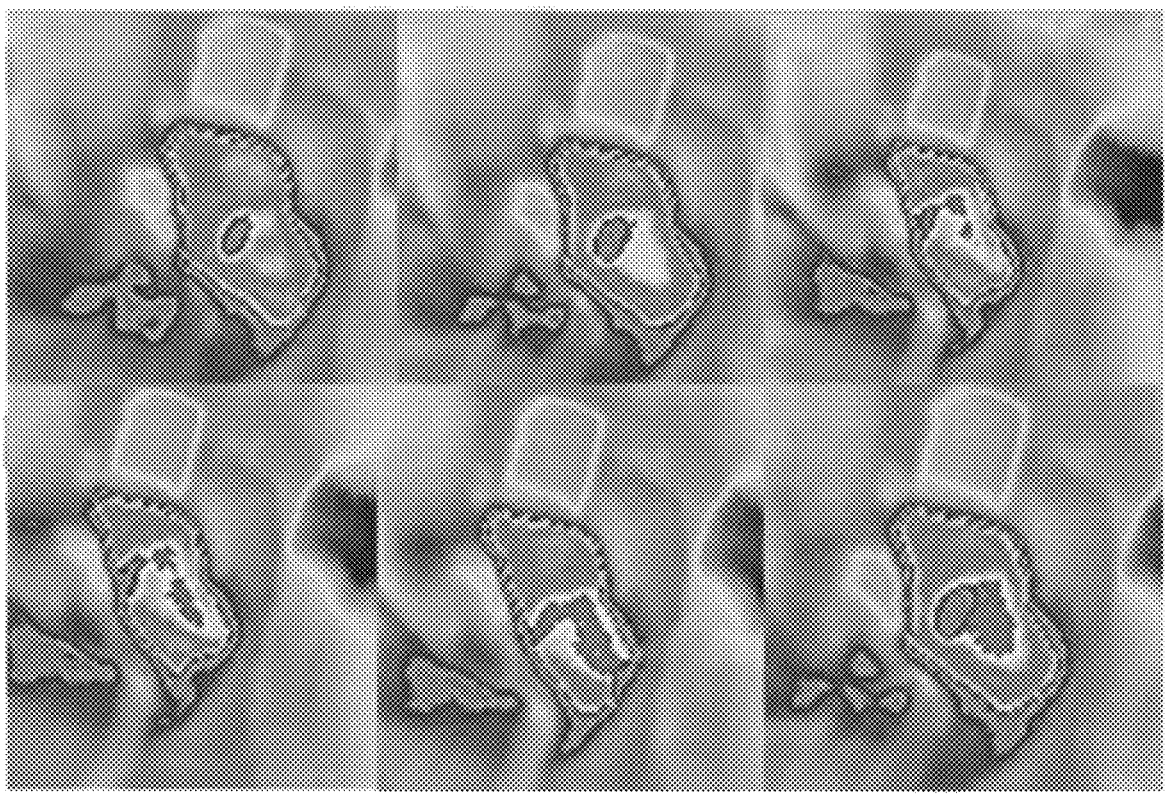

FIG. 11 shows the result of the image processing for detecting blood (shown by the blue color), during the contraction of the heart muscle of a rabbit, showing in real time through the chambers of the heart muscle (right atrium to the right ventricle).

Figure 12:
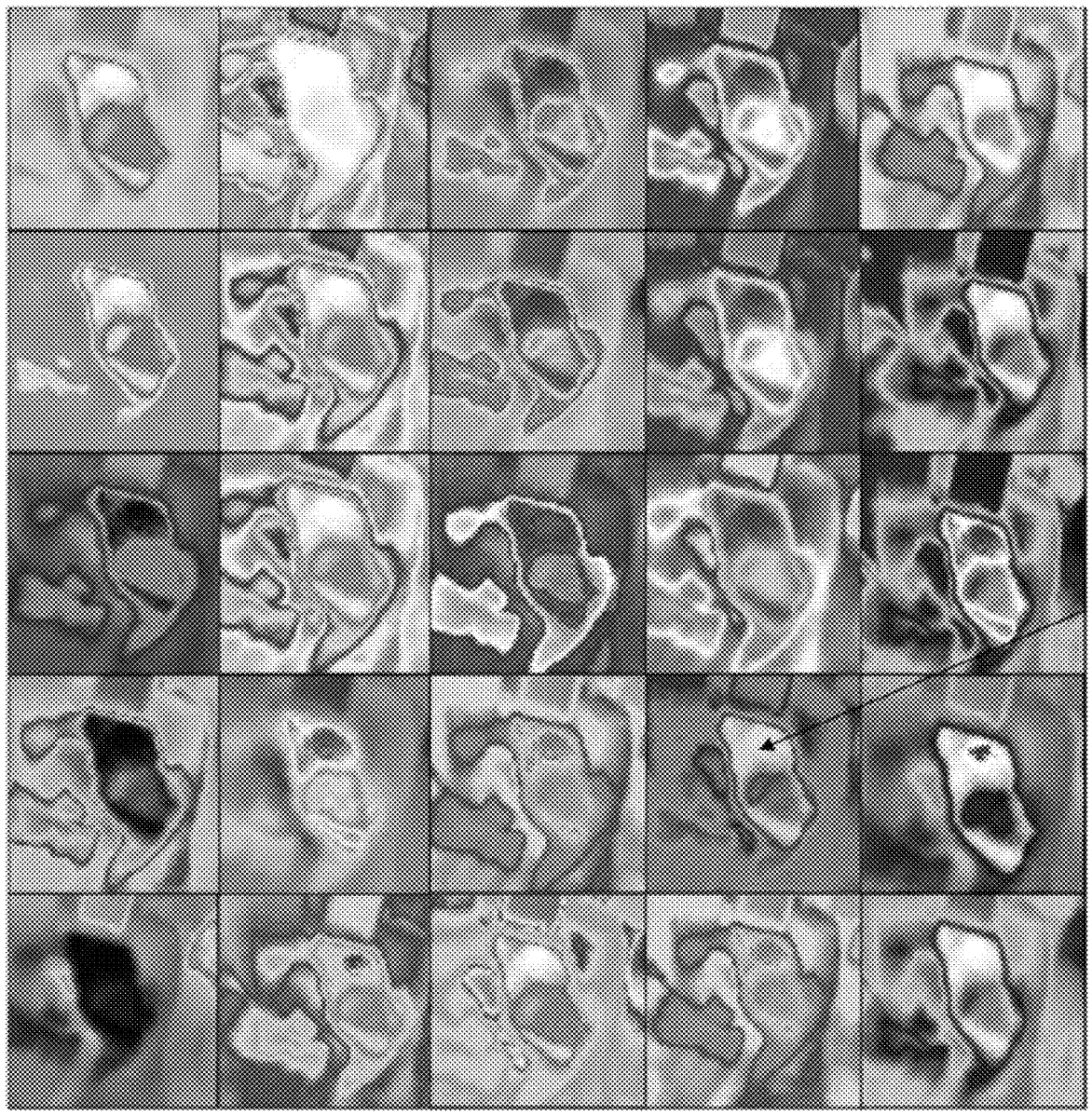

FIG. 12 shows the possibilities of image processing, viewed in real time, in different color palettes, in order to find the most suitable palette (indicated by the arrow), for resulting in the image in FIG. 11.

Figure 13:
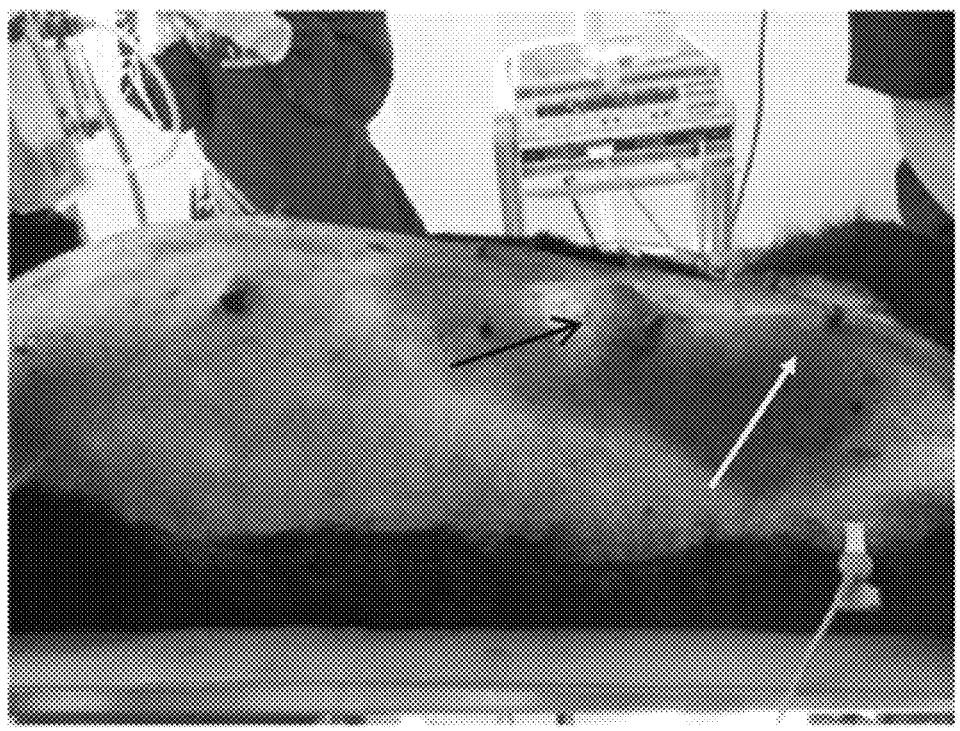

DEMONSTRATION of the DIAGNOSTIC POTENTIAL Standard from Proposed Thermometric Video Image FIG. 13: The black arrow indicates a visible tumor mass (complex adenocarcinoma with cystic and papillary areas), while the yellow arrow is apparently composed of normal canine breast tissue with no visible or palpable changes.

Figure 14:
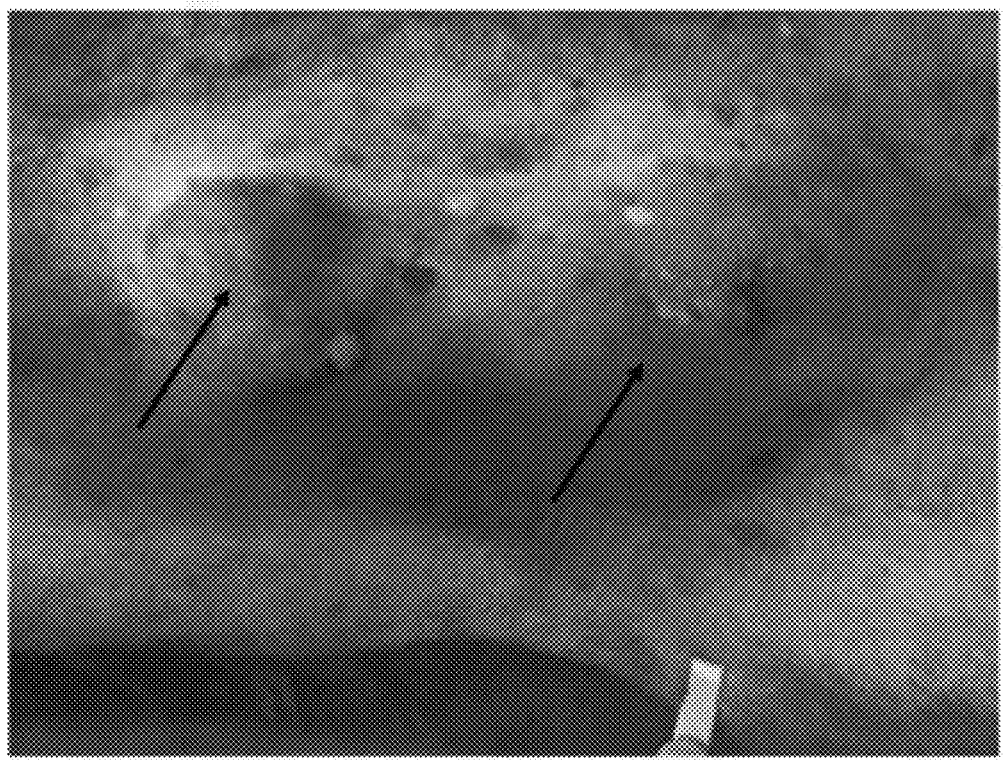

FIG. 14 shows an enlarged view of the FIG. 13.

Figure 15:
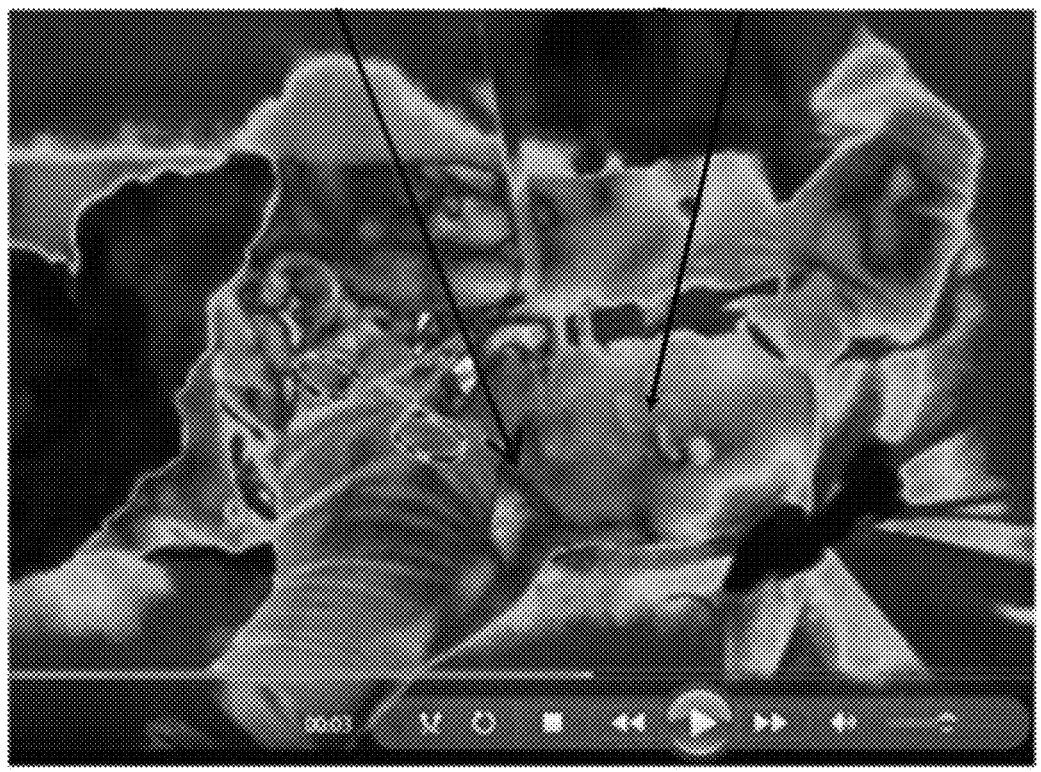

FIG. 15 shows images processed during the surgery, making FIGS. 13 and 14. The surgeon's hand holds the tumor mass (adenocarcinoma), indicated by the black arrow and on the right side there is a very evident, not visible or palpable rough texture during inspection (yellow arrow).

Figure 16:
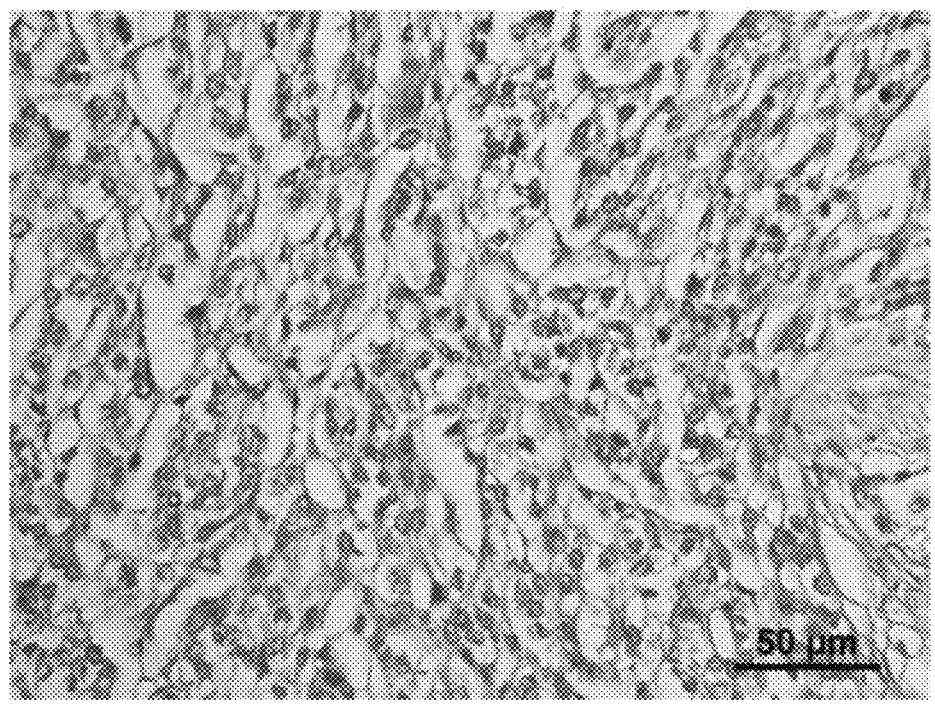

FIG. 16 shows a presumptive biopsy with histopathological result indicating a pattern similar to the tumor area (solid carcinoma).

Figure 17:
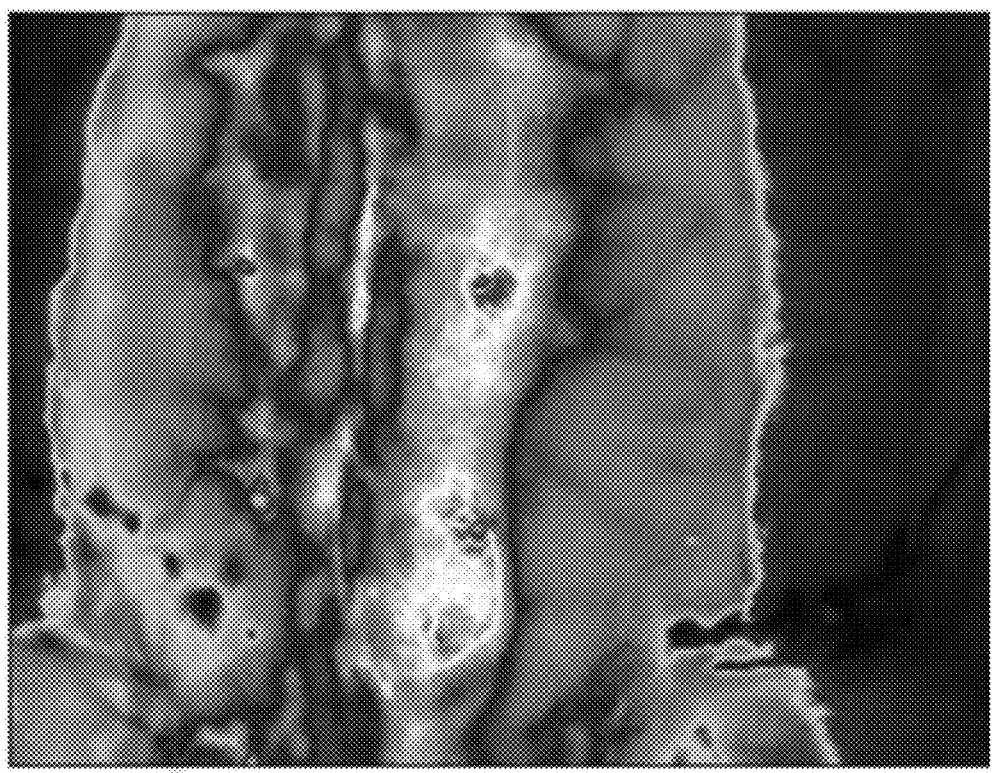

FIG. 17 shows contralateral asymmetry with areas with the same image pattern in a dog.

Figure 18:
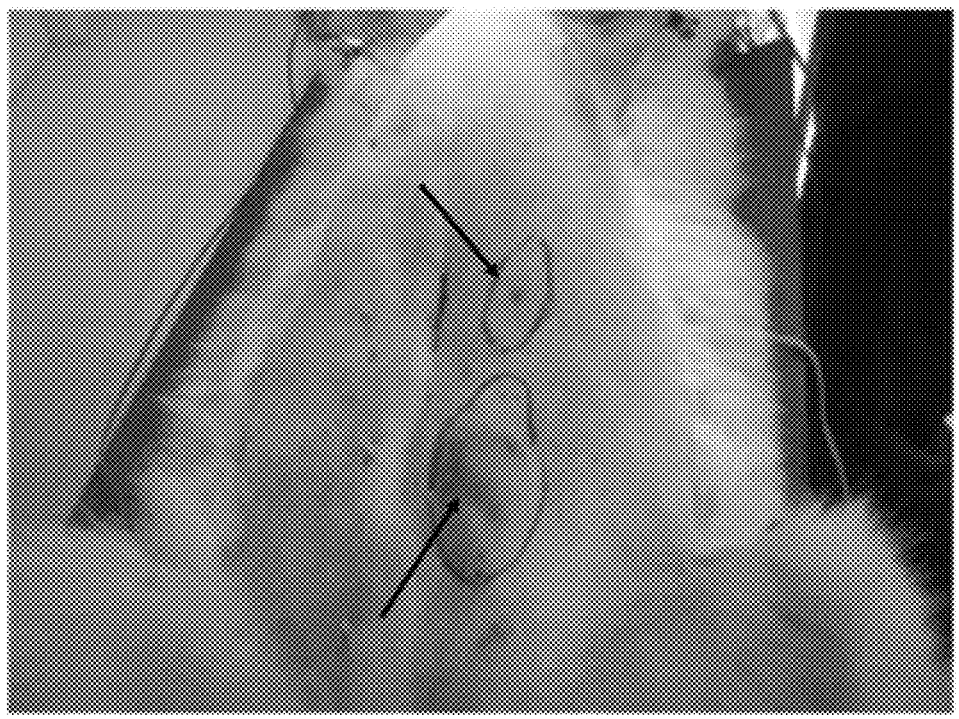

FIG. 18 shows the demarcation of the asymmetric areas. In the lower portion, the tumor mass is palpable and visible (black arrow), but the upper mark has no evidence of change (yellow arrow).

Figure 19:
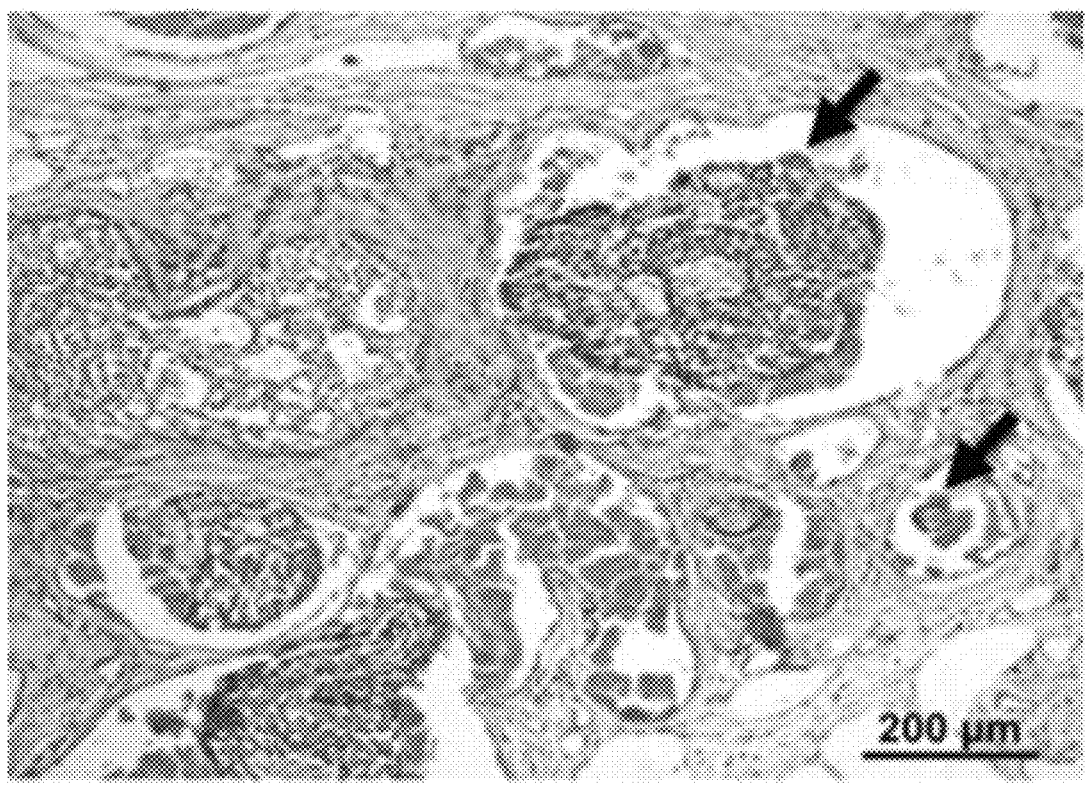

FIG. 19 shows a presumptive biopsy (yellow arrow) with a pattern similar to the tumor area indicating a metastasis (muciparous, solid and invasive patterns with vascular neoplastic emboli compatible with adenocarcinoma).

Figure 20:
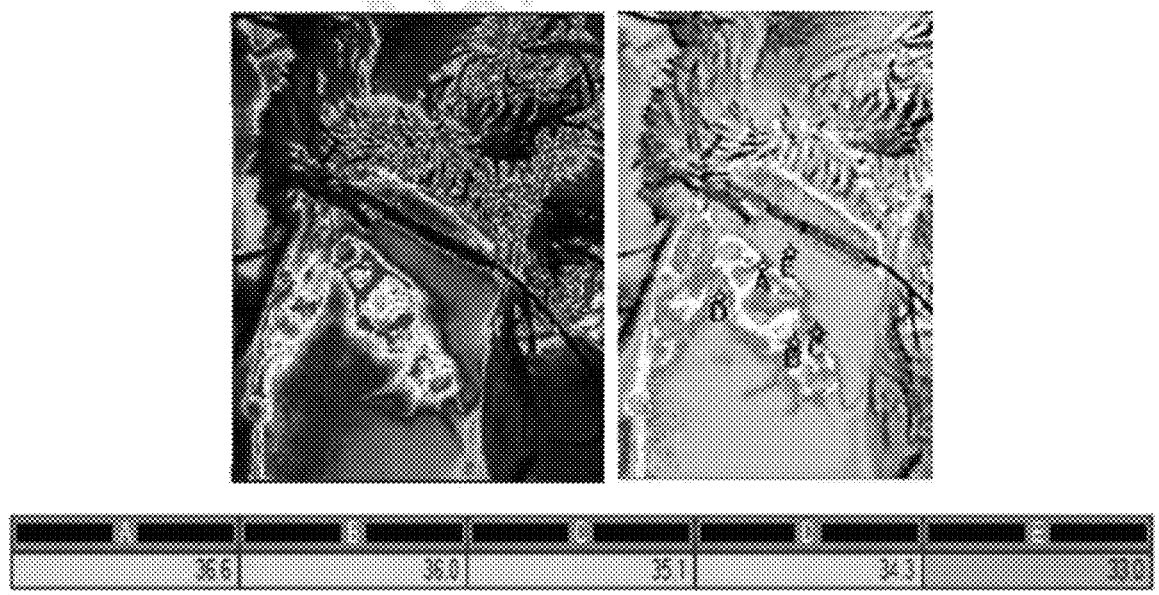

FIG. 20 shows that in the same area there may be a large temperature difference due to the neovascularization promoted by tumor (tubular adenocarcinoma), where the points are established by different temperatures (dog).

Figure 21:
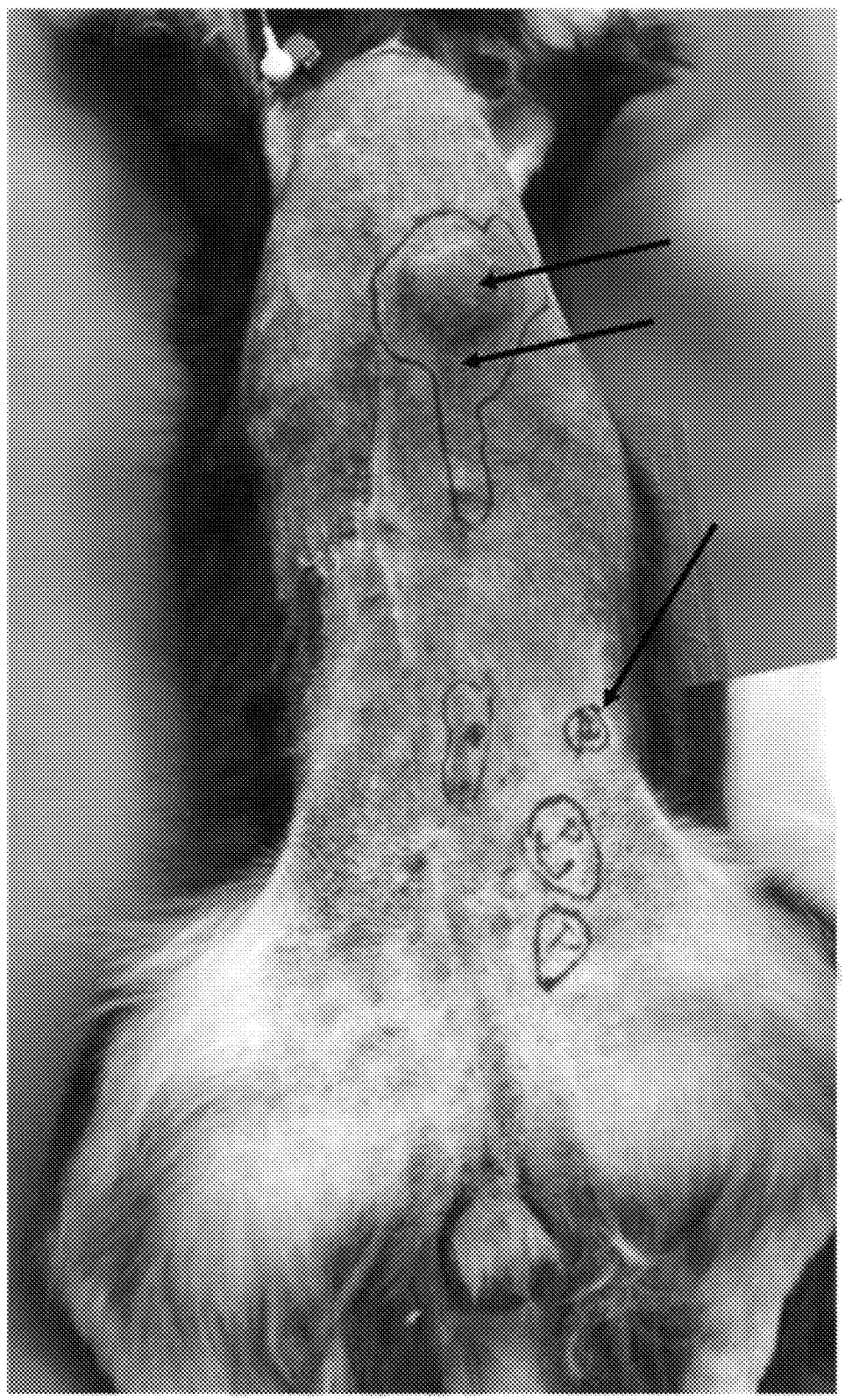

FIG. 21 shows the tumor mass (black arrow), the area of tumor coverage (red arrow) and presumptive area of metastasis at the distance (yellow arrow) in the dog.

Figure 22:

FIG. 22 shows the thermometric video image of FIG. 21 detecting the tumor coverage area.

Figure 23:
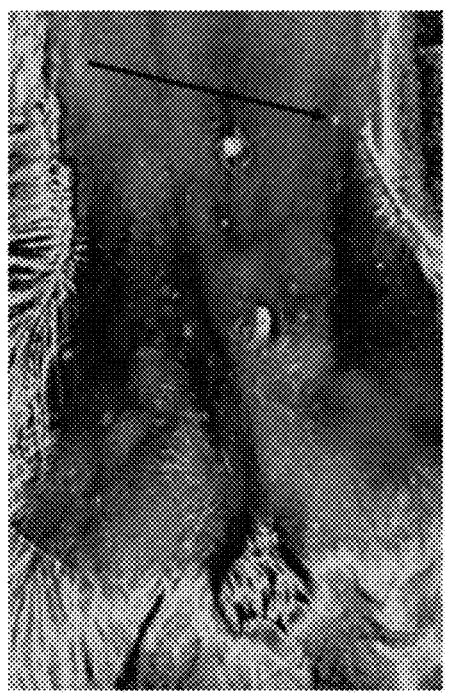
Figure 24:
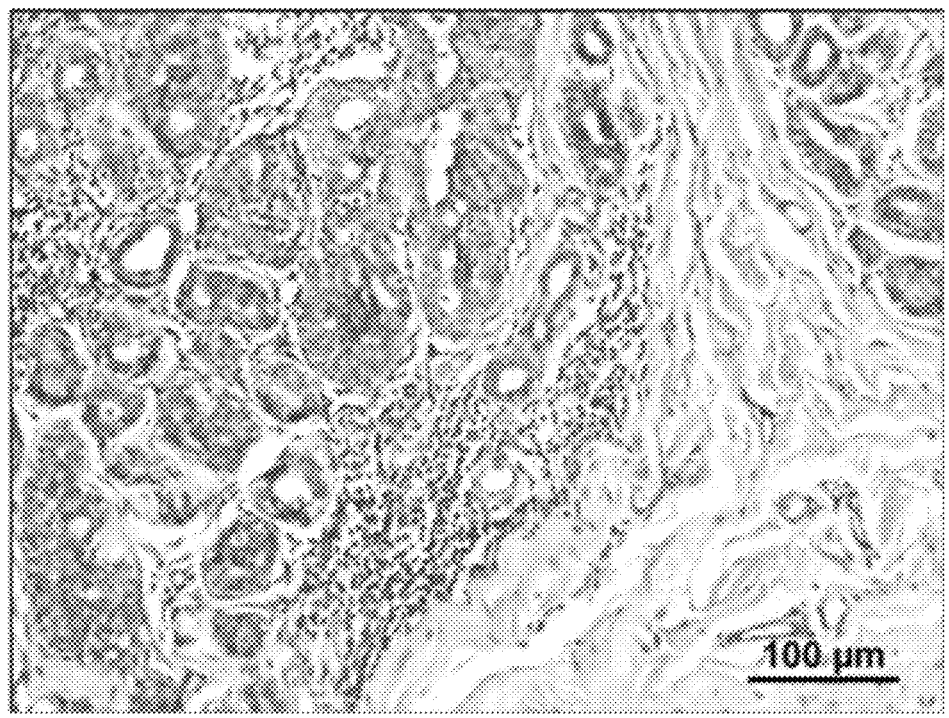

FIG. 23 shows the thermometric video image of FIG. 21 detecting a potential metastasis at the distance proved in FIG. 24.

FIG. 24 shows the result of the histopathological examination of the presumptive area of FIG. 21 (yellow arrow) resulting in a tubular carcinoma.

Figure 25:
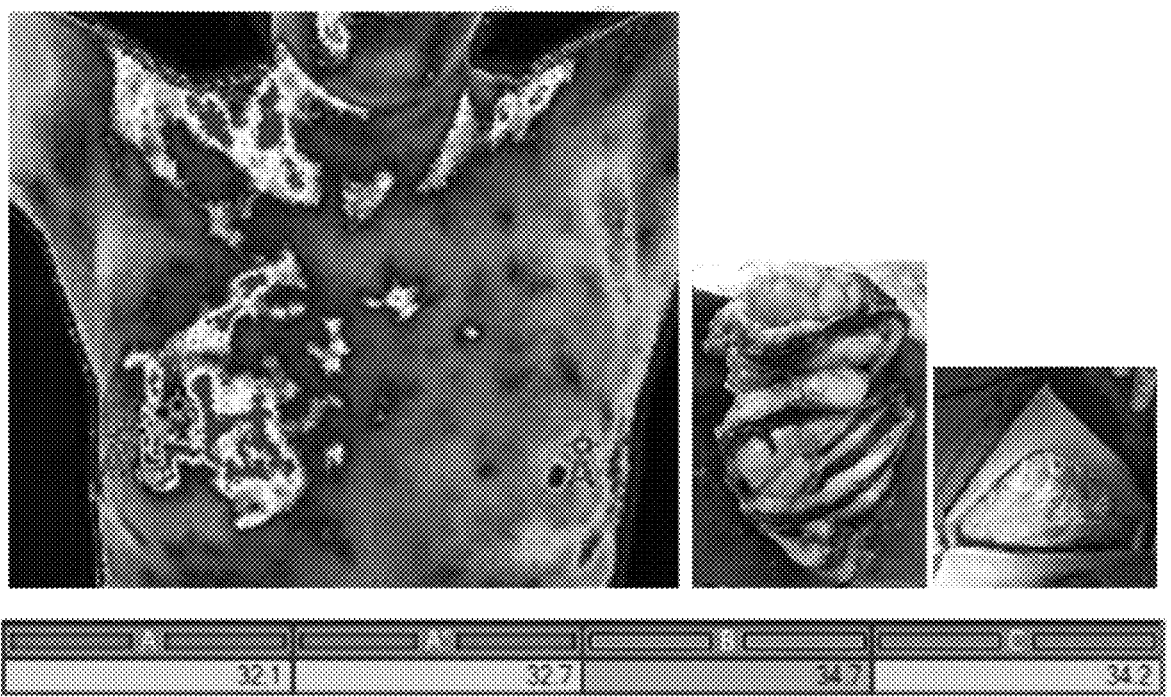

FIG. 25 shows the asymmetric area in the upper internal quadrant of the human right breast and a change in low temperature, indicating dysfunction. In the center, a surgical piece containing a sarcoma removed from the area delimited by thermometry video. On the right, there is a demonstration of the removed area.

Figure 26:
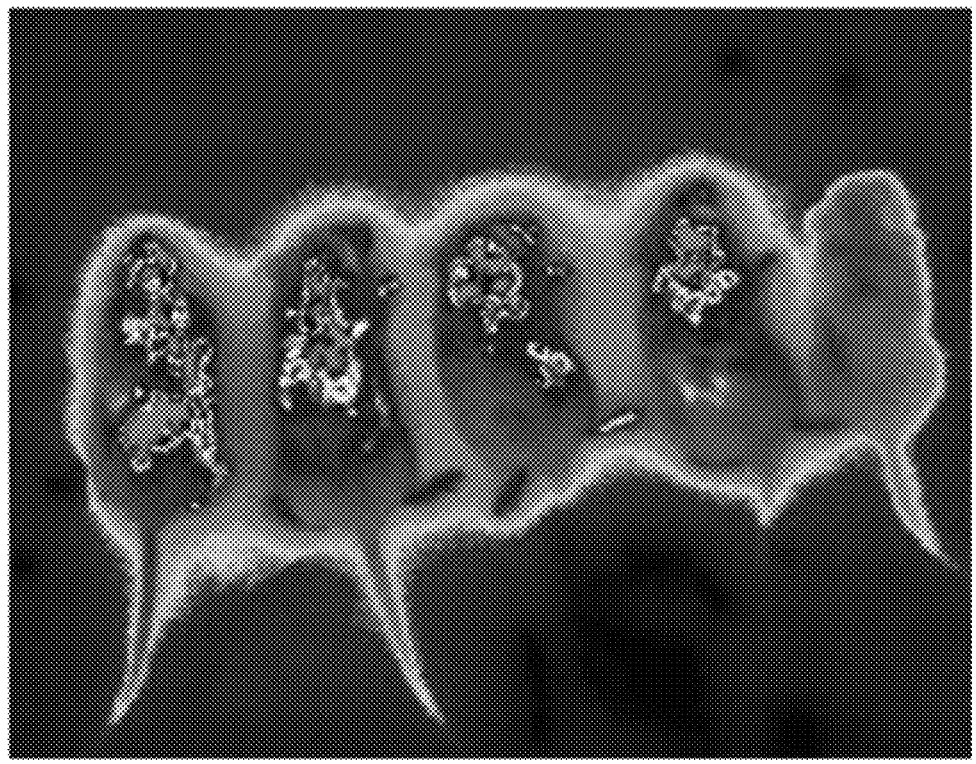
Figure 27:
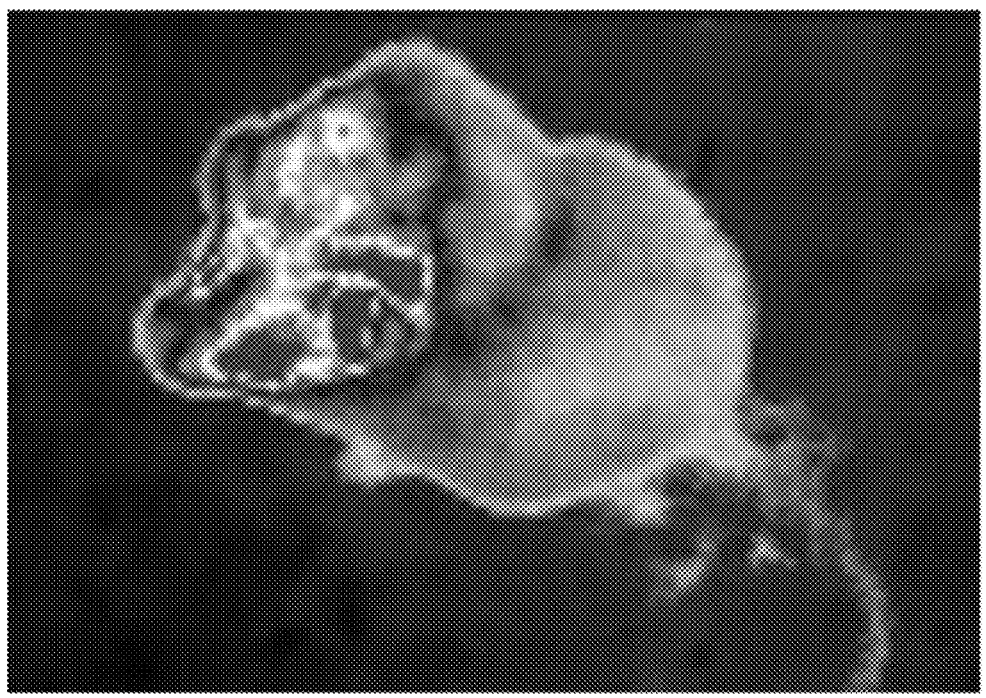

FIGS. 26 and 27 show the areas affected by the melanoma induced in rats.

Figure 28:
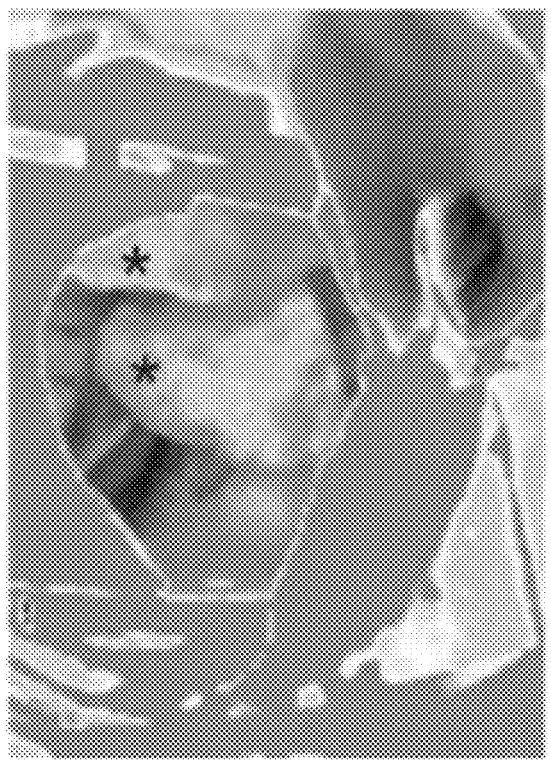
Figure 29:
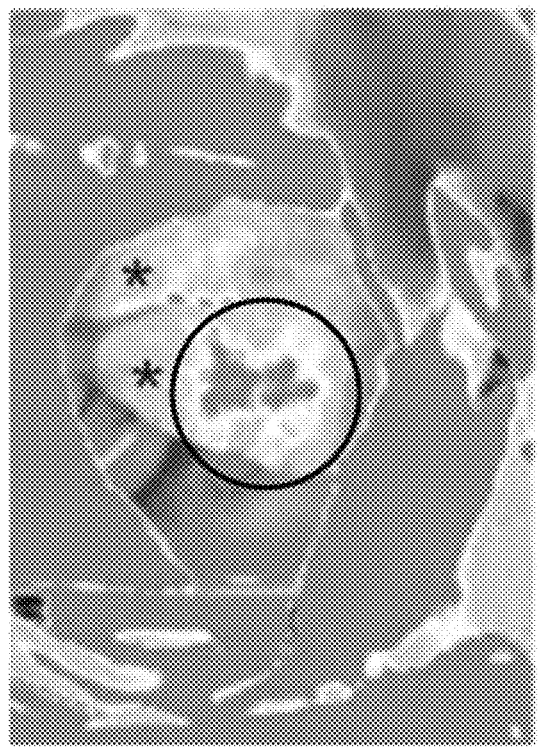
Figure 30:
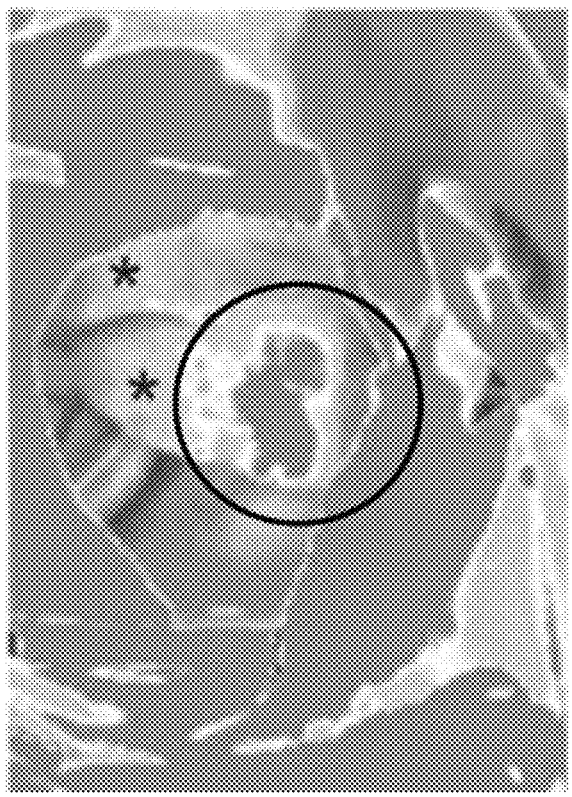

FIGS. 28, 29 and 30 show images of the medium (*) and cranial right pulmonary lobe in sequential inspiratory movement, highlighting the breathing movements of air inlet in the demarcation by circles.

Figure 31:
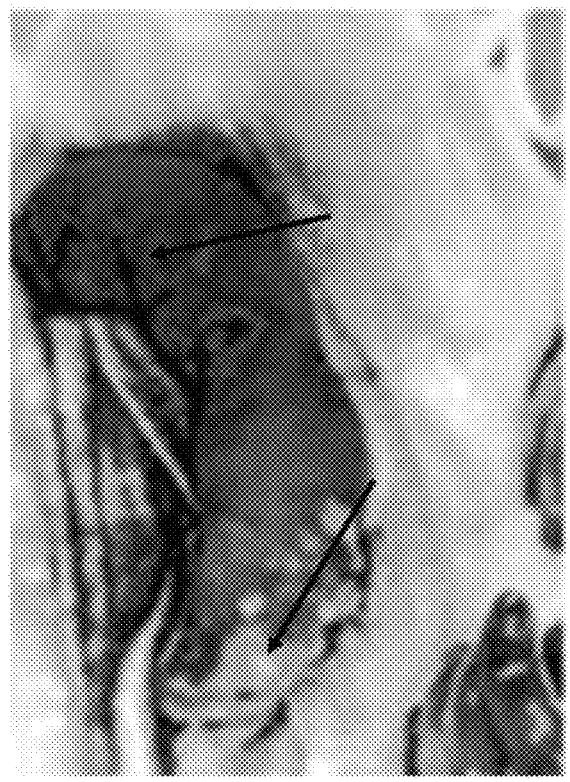

FIG. 31 shows an image of the distended loop of the intestine (colon) by impaction of a fecaloma showing the vascularized area (black arrow) and the devitalized area (yellow arrow).

Figure 32:

FIG. 32 shows an image of the distended loop of the intestine (colon), showing the visualization of the circulatory anatomy of the mesentery (*).

Figure 33:
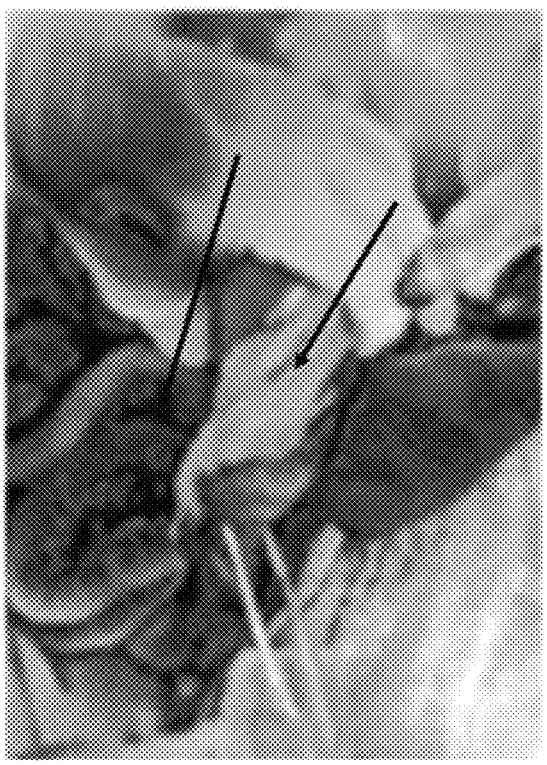

FIG. 33 shows a devitalized area of the colon (yellow arrow) and circulatory anatomy of the mesentery (black arrow) of a dog.

RESULT of the Proposed Standard of Thermometric Video Image

FIG. 34 shows a real image of the liquid leakage of lymph into the thoracic cavity (around the lung and heart), during a surgery in a dog.

FIG. 35 shows the thermometric image in FIG. 34 with the color palette of the industrial standard rainbow, inserted as a comparison standard to contextualize the image enhancement by the new standard.

Figure 36:

FIG. 36 shows an embodiment of the image through a color palette capable of demonstrating the site of the lymph leakage by the thoracic duct.

Figure 37:

FIG. 37 shows an embodiment of the image, through a color palette, the compressive clamping to interrupt the flow from lymph through the thoracic duct.

Figure 38:
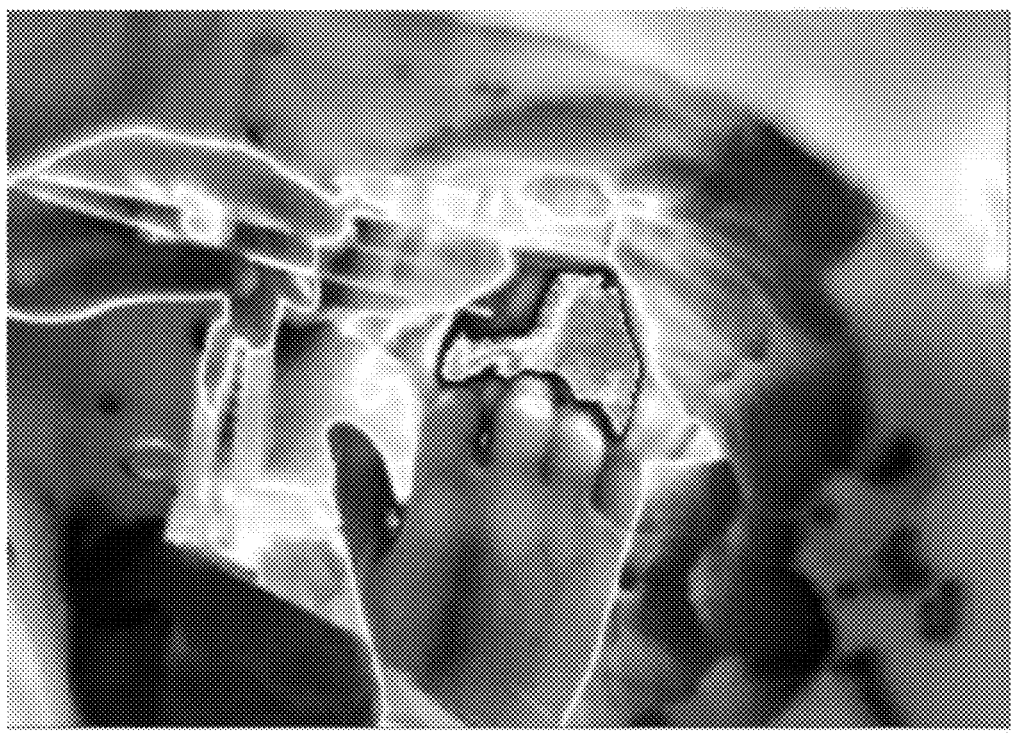
Figure 39:
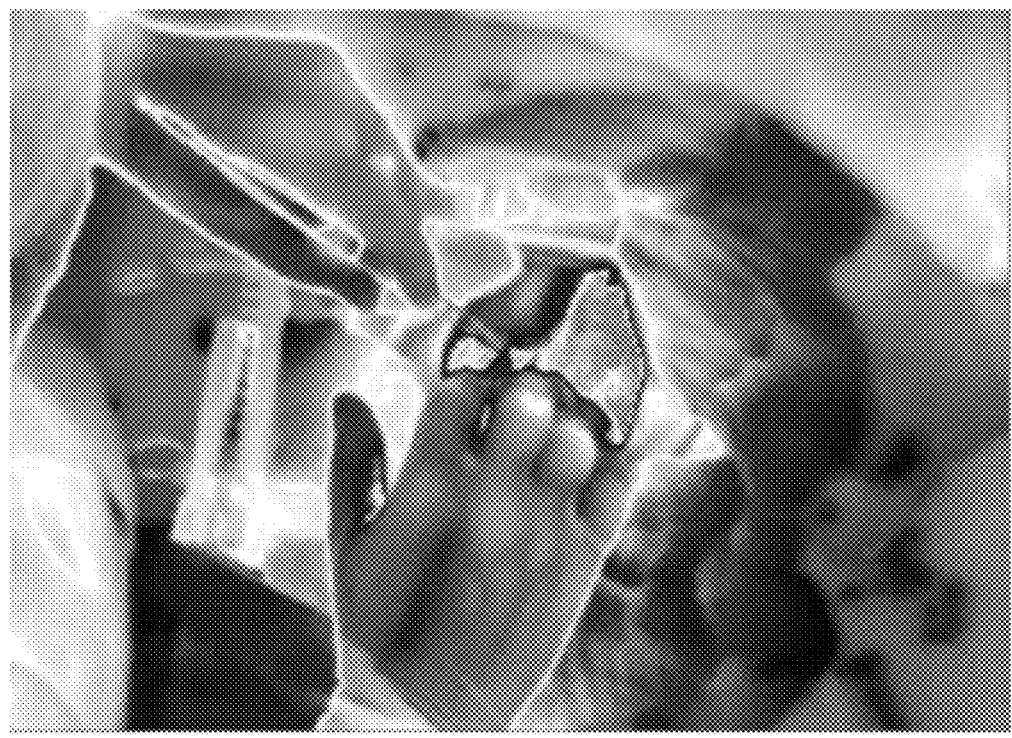
Figure 53:
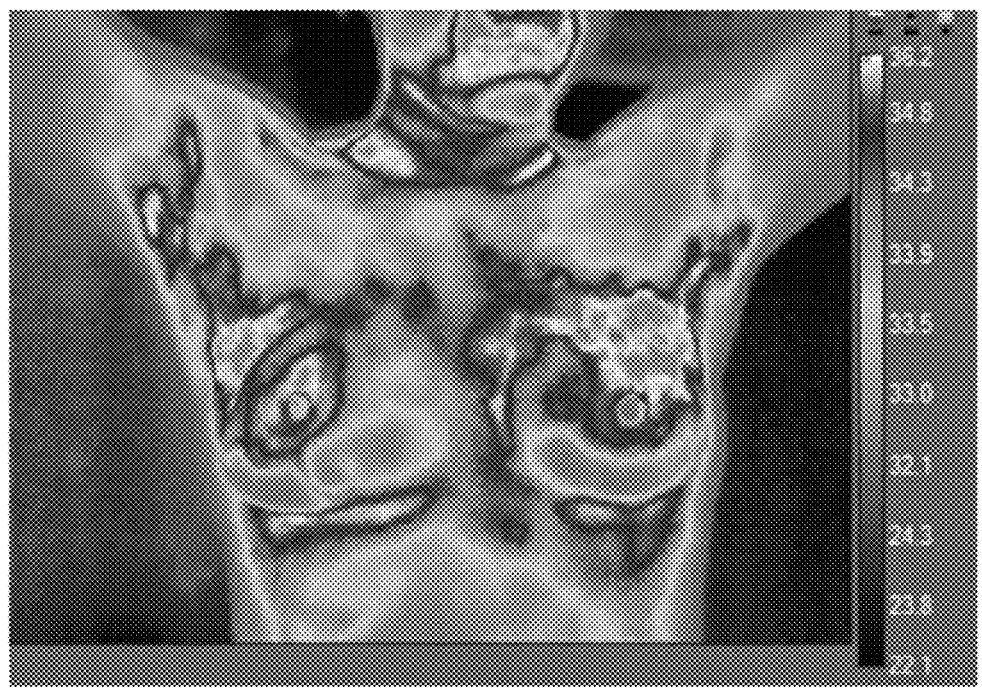
Figure 54:
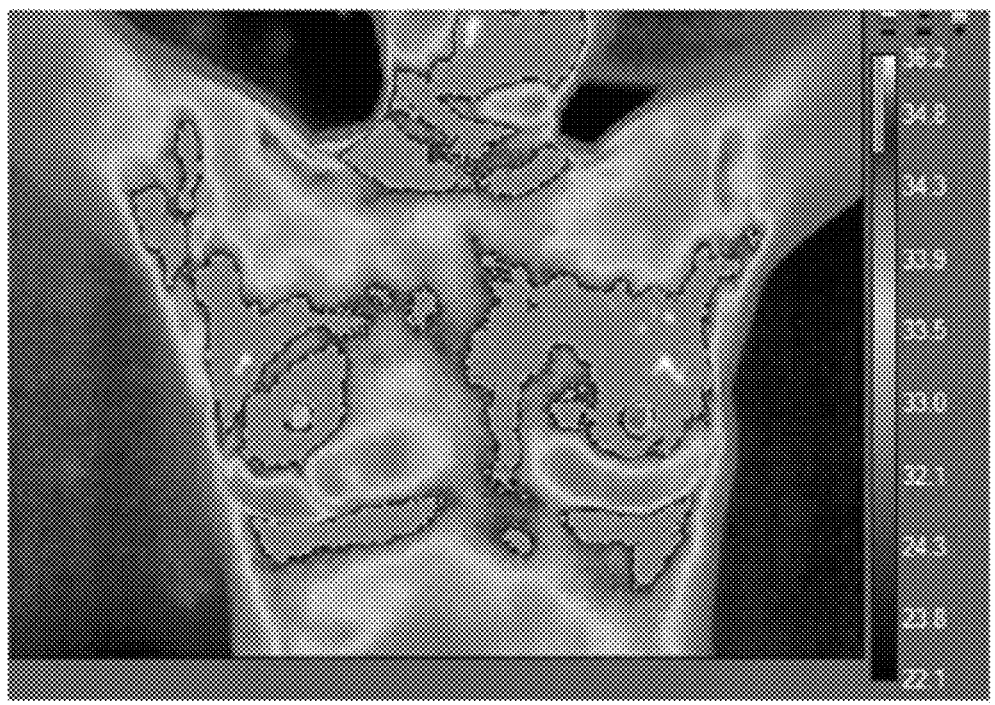
Figure 55:
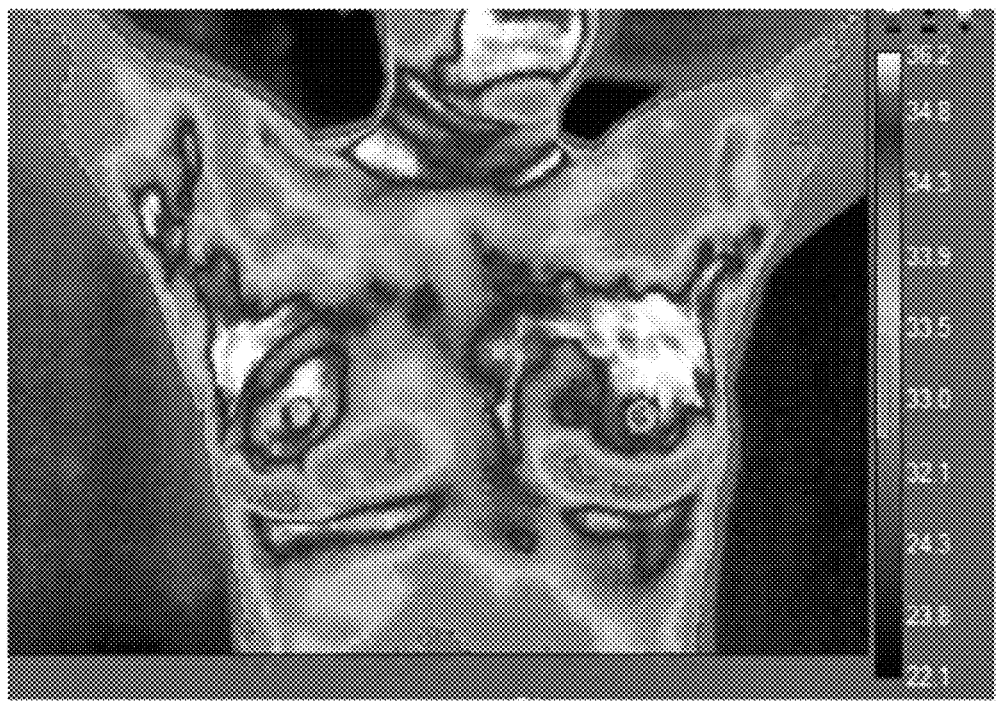
Figure 56:
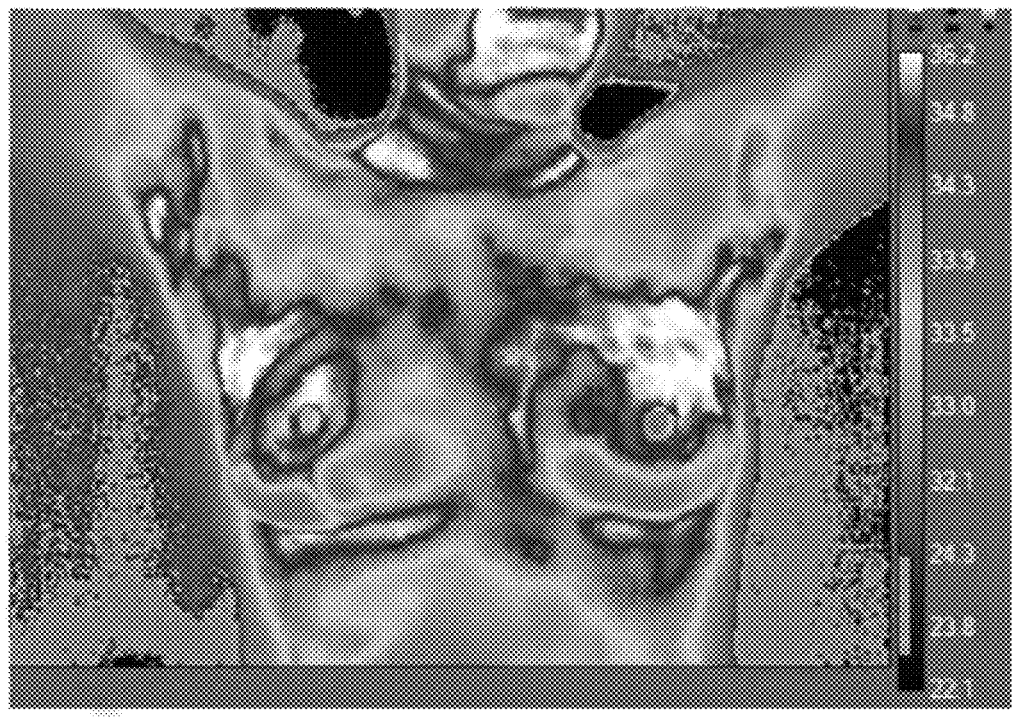

FIGS. 38 and 39 show embodiments of an enhancement of the images in FIGS. 36 and 37, respectively, after a new processing as the construction of palettes refines the process.

CONSTRUCTION of the Proposed Standard of Thermometric Video Image

For industrial inspection, it is justifiable to obtain information on all temperatures emitted by the object, since it tends to enter thermal equilibrium, but for human being what matters is the temperature difference between pixels or areas in relation to its surroundings, i.e., greater or lesser metabolic activity indicating dysfunction, since we are homeothermic and keep our internal temperature constant.

Peripheral temperature can vary uniformly with the environment, but in a pathologic instance, we have a temperature difference between pixels that can reach degrees. Hence the importance of sensitivity of the equipment to be used and the gathering of the temperatures that interests us, according to the pathology to be studied.

By using FIGS. 38 and 39 as an example, where the object of study is the lymphatic tissue (lymph), where the temperature range to be studied is slightly below the maximum temperature (blood). In this case, the palette must be built to show the highest temperatures, while the temperatures that do not interest us should form a discreet color gradient, the gray scale being the most ideal.

FIG. 40 shows another embodiment of the color palette used in the edited images, where different colors at the maximum peak of the gray scale promote the visualization of different tissues.

FIG. 41 shows another embodiment of the color palette used in the edited images, where different colors at the maximum peak of the gray scale, with a strong color impression before the maximum peak, it demonstrates the area of greatest metabolic intensity.

FIGS. 42, 43 and 44 show another embodiment of the color palette used in the edited images, where a change in the palette construction can change the result of the image, adding details or confusing the operator while working in real time.

FIG. 45 shows another embodiment of the color palette used in the edited images, where the gray scale, with the addition of another color in the middle portion in gradient up to the limit before the peak coloring, promotes visualization of the surroundings of interest area.

FIG. 46 shows another embodiment of the color palette used of the edited images, where as it abandons the gray scale as a background tone, the uniform gradient can be confused in a real-time examination.

FIG. 47 shows another embodiment of the color palette used in the edited images, where a gradient with contrast in the gradient of tones can give information about the surroundings.

FIGS. 48 and 49 show another embodiment of the color palette used in the edited images. The inversion of the contrast area can be the difference between the visible image and the subjective image.

FIGS. 50 and 51 show another embodiment of the color palette used in the edited images, where the location of the concentration of colors contrasting with the gray scale can be the difference between the visible image and the subjective image.

FIG. 52 shows the use of segmentation to cancel information that does not matter, thus facilitating the analysis of the region of interest. In the temperature bar, the amplitude of the upper or lower segmentation defines the coverage of the region to be delimited.

FIGS. 53, 54, 55 and 56 show isotherms as demarcation resources used in regions of interest for facilitating the location of similar areas. According to the position and isotherm amplitude (in yellow) in the temperature column, the result produced seeks thermal similarity.

Figure 57:
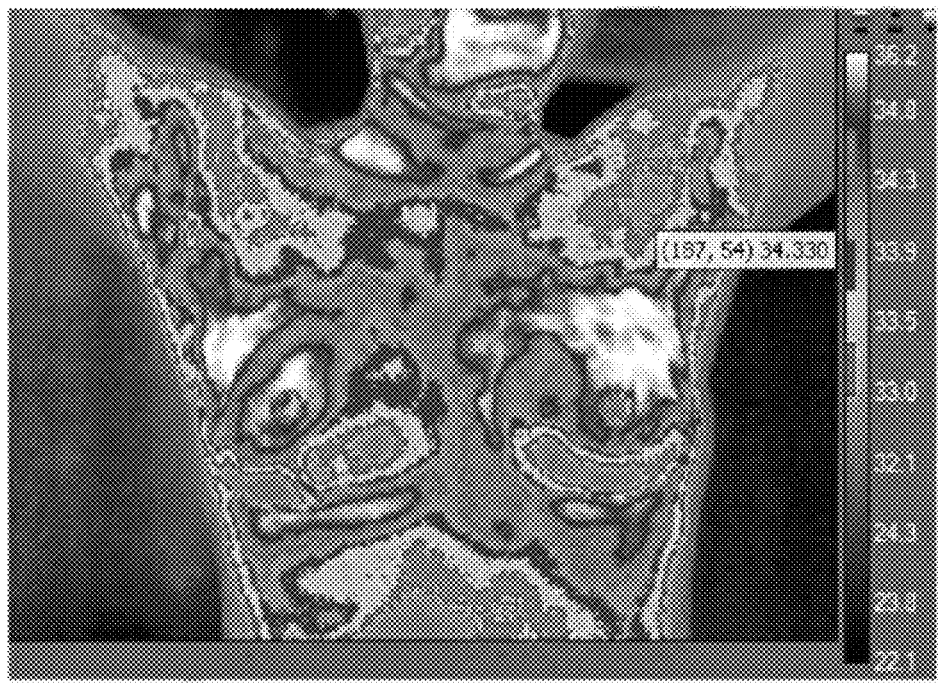

FIG. 57 shows several isotherms being used to identify thermal similarity, being useful on the search for pathological patterns when delimiting an area or searching for the same pattern at a distance from the evident pathology.

The Modular Environment for Algorithm Application

Figure 58:
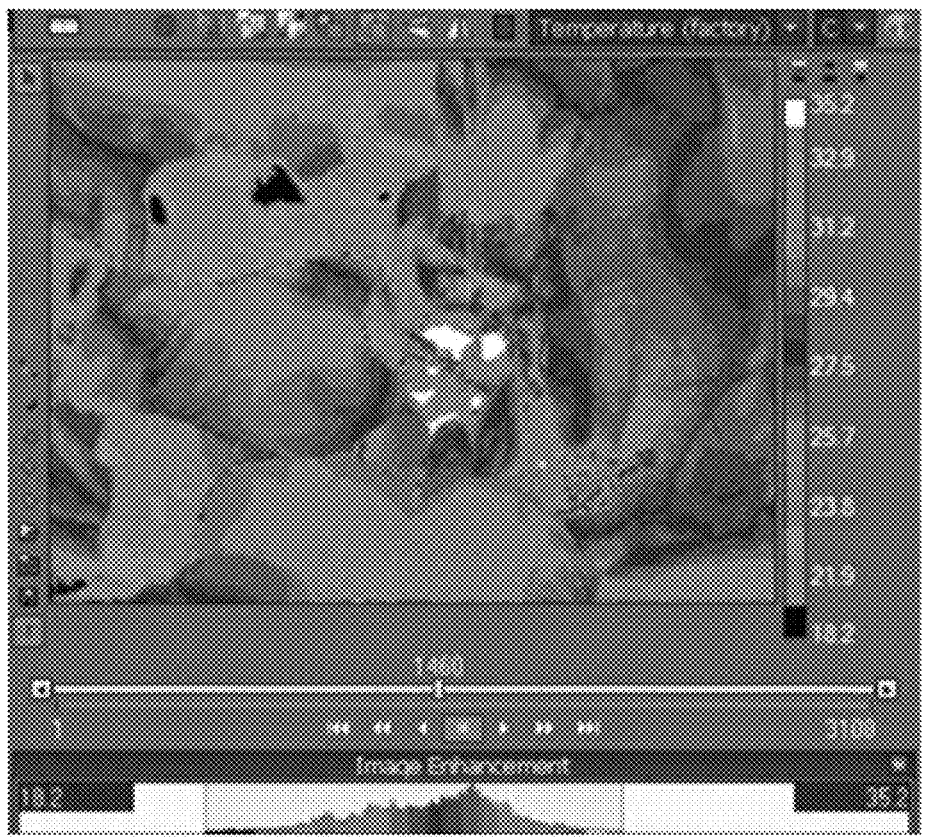

FIG. 58 shows an embodiment of the system in operation using the standard palette.

Figure 59:
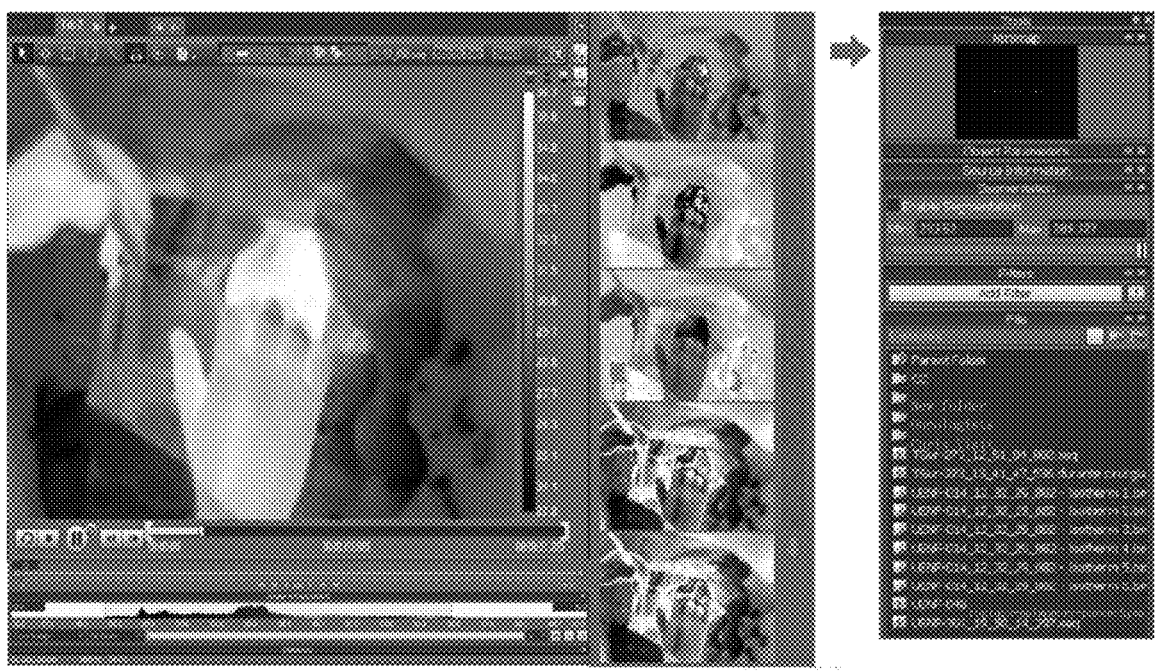

FIG. 59 shows an embodiment of one of the functions of the color palette search system with multiple color palettes available during real-time system operation. It should remember that these palettes have a uniform gradient background.

Figure 60:
Figure 61:
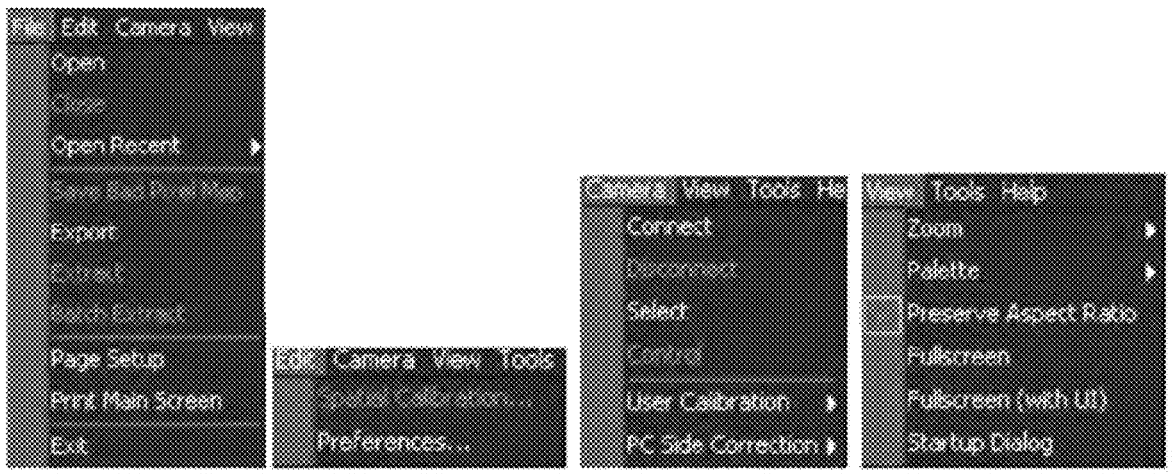
Figure 62:
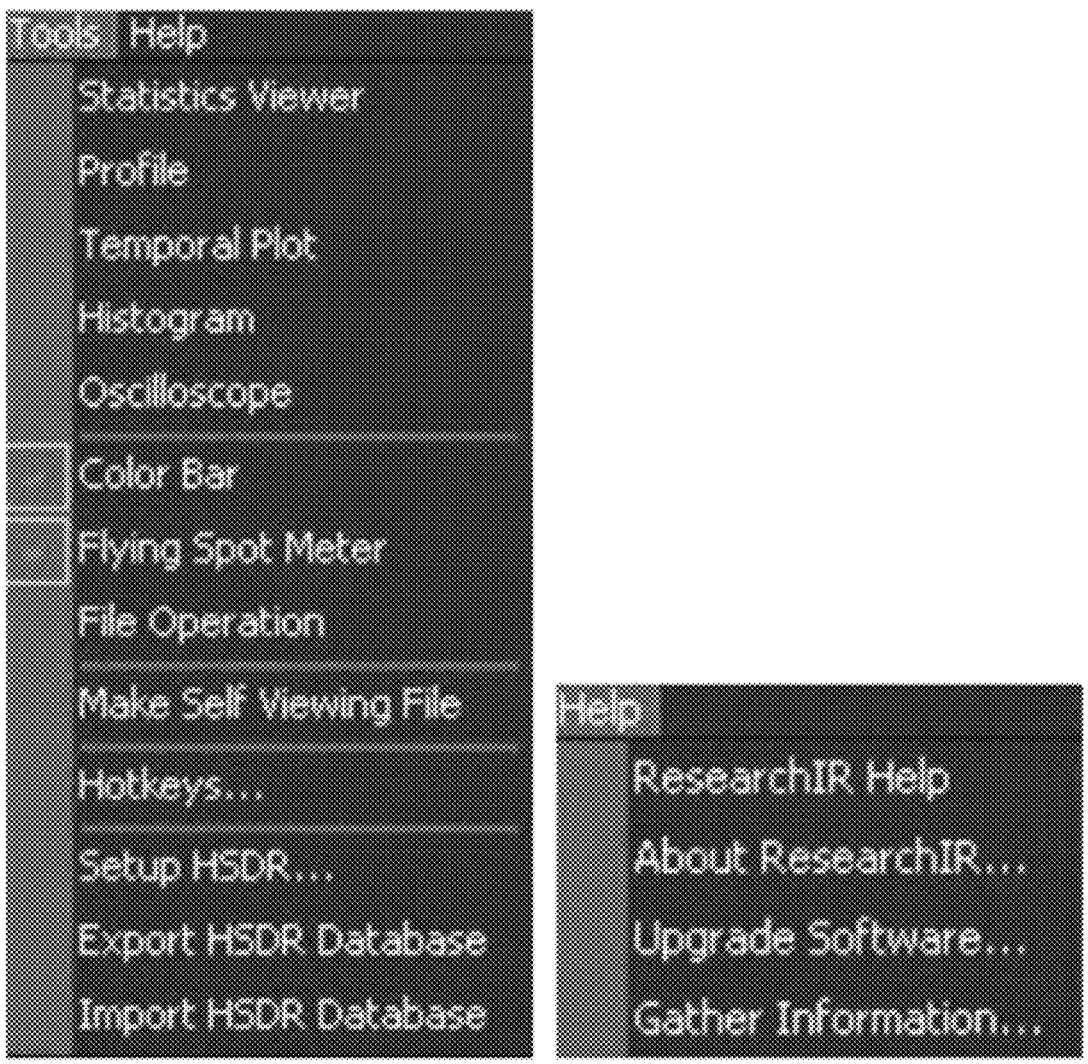
Figure 63:
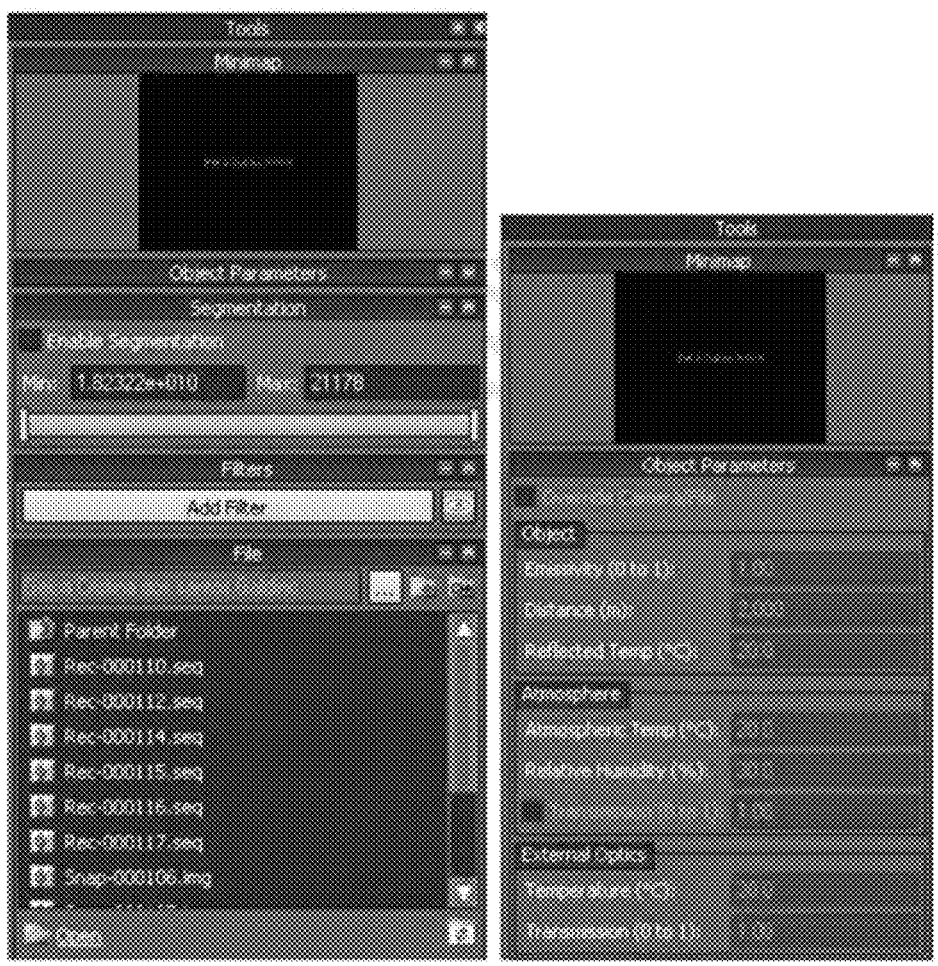

FIG. 60 shows an embodiment of the use of a system functionality to improve the image by the "Merlin bar" tool.

On a uniform gradient background, it is possible to group the set of colors in the palette (represented by a sequence of colors) and slide it over the uniform background, vertically, on the temperature bar until the image appears and becomes clearer. The "Merlin bar" tool allows small temperature differences to be evident by the color sequence, forming the image. The grouped color sequences of the palette are predefined colors, which become mobile over a uniform gradient color (with several pre-established patterns and that can be selected). In addition, isotherms (solid and isolated colors) also move in the vertical temperature bar for searching temperature changes in the search of asymmetries. For example, the choice of the 0.3° C. isotherm seeks out discrepant areas of 0.3° C. in relation to its position in the vertical temperature bar, pointing out areas to be investigated.

Technology Association

Figure 64:
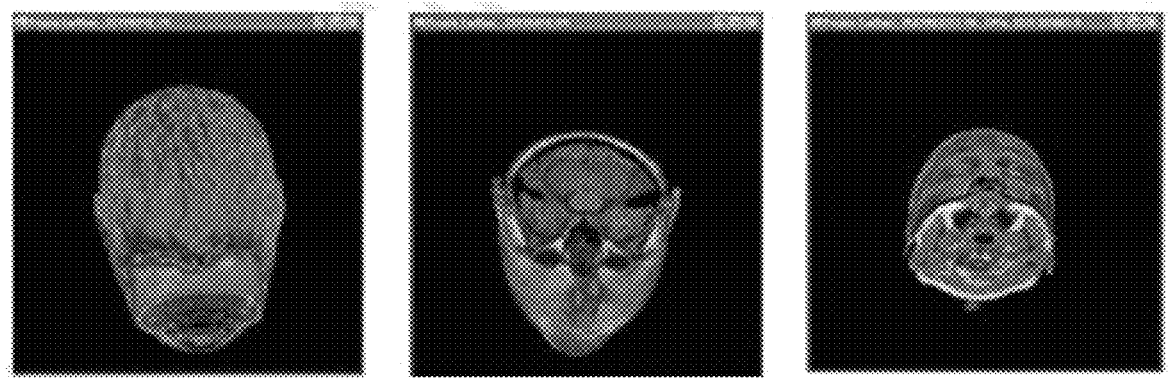

FIG. 64 shows an embodiment of a 3D reconstruction from thermal images and nuclear magnetic resonance.

FIG. 65.a and 65.b show that radiometric images allow new processing as the technology advances. FIG. 65.a was processed at the beginning of the development of the technique and FIG. 65.b, a year later, since the processing logic was repeated continuously. Indicated by the black arrow, the tumor mass detected in both images and on the right side in FIG. 65.b there is a very evident, not visible or palpable rough texture during the inspection (yellow arrow).

Figure 66:
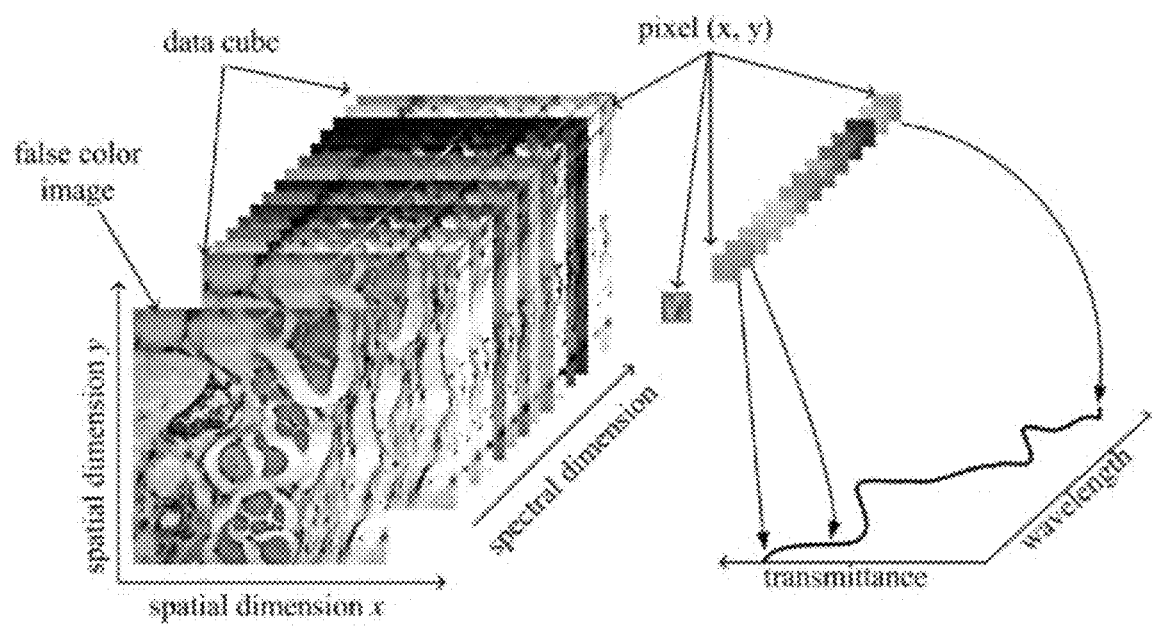

FIG. 66 shows the concept of the spectral data cube. The cube data contains two spatial dimensions and a spectral dimension (LI et al., 2013) for the diagnosis of presumptive areas of alteration, but without visible or palpable signs.

Figure 67:
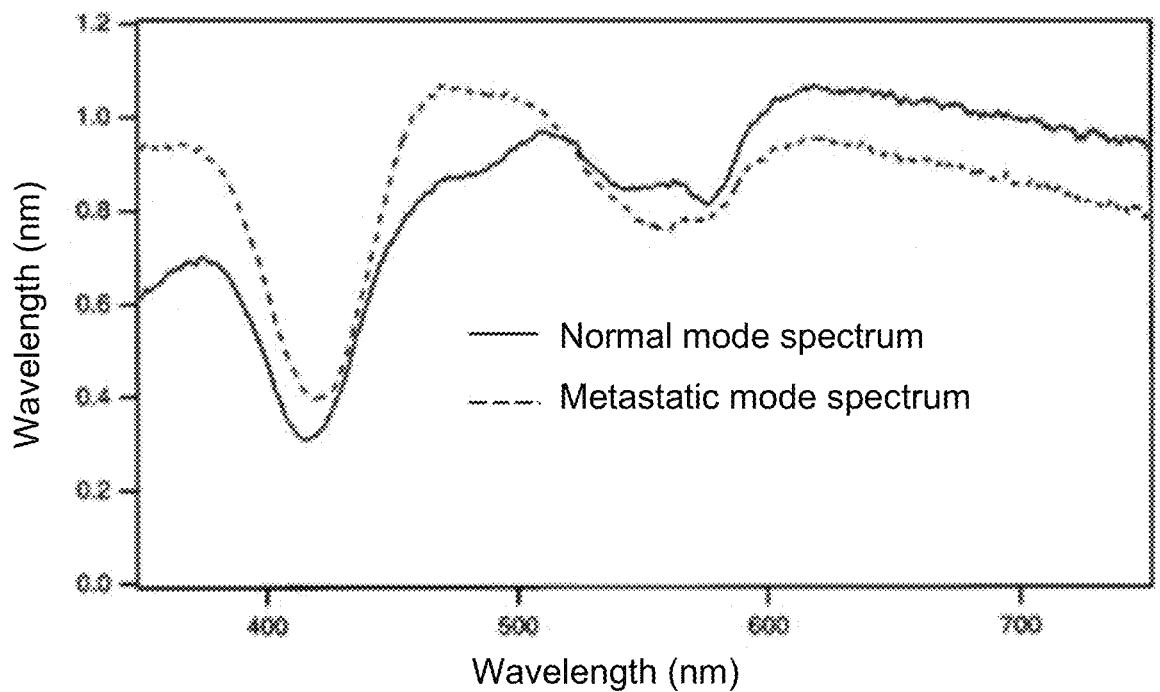

FIG. 67 shows normal spectral and metastatic result of the sentinel lymph node (O'SULLIVAN, 2011).

Figure 68:
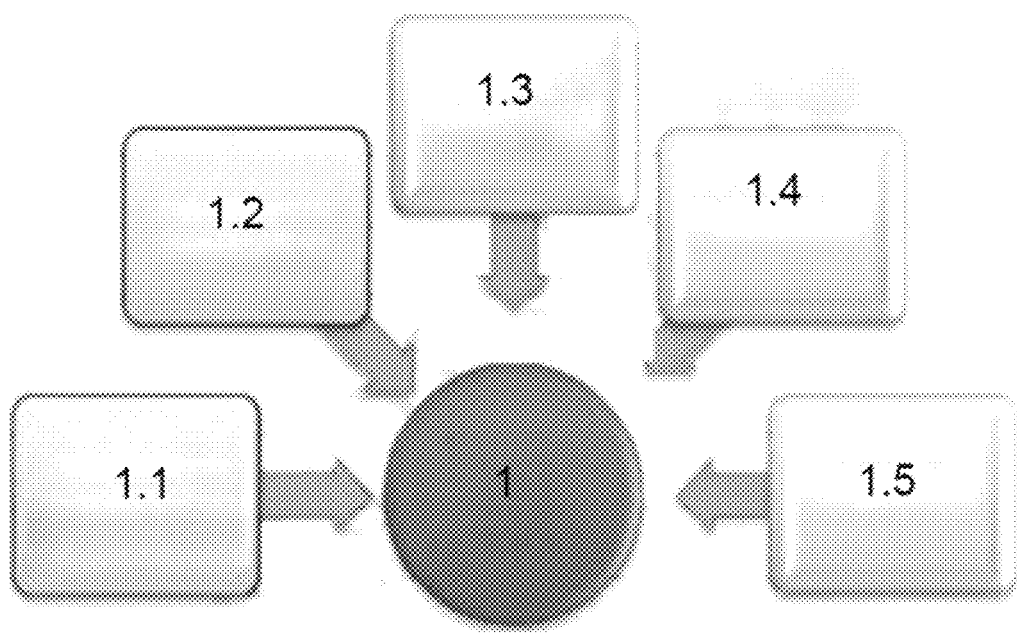

FIG. 68 shows an embodiment of the system for processing thermometric video images, which can be used in several technological fields.

Figure 69:
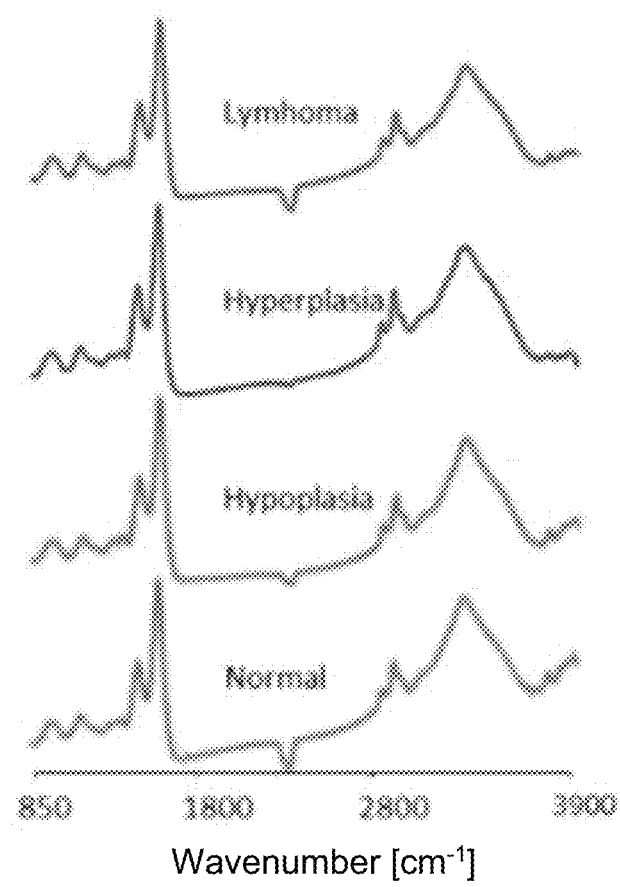

FIG. 69 shows an example of spectra obtained from the NIR image when using the "Spectral" tool.

DETAILED DESCRIPTION OF PREFERRED EMBODIMENTS

The following descriptions are presented by way of example and are not a limitation to the scope of the invention, and they will make the object of the present patent application be more clearly understood.

In a first object, the present invention presents a method of processing thermometric video images of patients comprised of the steps of:
a. delimitation of the region of interest and registration of anomalies not visible to the naked eye, through the emission of electromagnetic waves MIR and LIR;
b. thermometry video of the region of interest through the emission of electromagnetic waves MIR and LIR;
c. identification of anomalies not visible to the naked eye for spectral analysis of the sample through the emission of NIR electromagnetic waves;
d. adjustment the resolution of the generated video thermogram.

The length of the infrared radiation is within a range of 0.75-1000 μm, it can be subdivided into three smaller groups: near-infrared or NIR (0.76-1.5 μm), medium infrared or MIR (1.5-5.6 μm) and far infrared or FIR (5.6-1000 μm). Although infrared emissions from human skin at 27° C. are within wavelength range from 2 to 20 μm, it peaks at around 10 μm. The wavelength range between 8-12 μm is called body infrared radiation, however, with the new generations of detectors, the NIR and MIR regions are also being used (LAHIRI, 2012).

Emissivity is the relationship between the energy radiated (at a given wavelength) by any body and a black body at the same temperature. Thus, the emissivity always assumes values between 0 and 1 being numerically equal to the fraction of the radiation absorbed by the body. This heat is invisible to the optical receptors of the retina, but it can be captured by special detectors generating hyper or hyporadiant images.

The heat emitted by the human body (infrared rays) is generated by molecular movement. This heat is continuously produced by the body, being a product of the metabolism (result of the total biochemical reactions of the organism), while the metabolic intensity expresses the release of heat during the chemical reactions.

While the peripheral temperature varies with circadian rhythm, physical effort, metabolism, hydric balance, drugs and ambient temperature, the central temperature does not change (homeothermia), being uniform and resulting in symmetry in the thermal patterns.

A healthy person has thermal symmetry between the left and right sides of the body, with a small difference in skin temperature on both sides of the human body, around 0.2° C. (UEMATSU, 1985).

For industrial inspection, it is justifiable to obtain information on all temperatures emitted by the object, since it tends to enter thermal equilibrium, but for humans only extreme temperatures are important, since we are homeothermic and we maintain our internal temperature constant.

The peripheral temperature may vary with the environment uniformly, but in a pathology instance, we have a temperature difference between pixels that can reach degrees. Hence the importance of the sensitivity of the equipment to be used and the capture of the temperatures that interests us according to the pathology to be studied.

By using FIGS. 38 and 39 as an example, where the object of study is the lymphatic tissue (lymph), where the temperature range to be studied is slightly below the maximum temperature (blood). In this case, the palette is built to show the highest temperatures, while the temperatures that do not interest us form a discreet color gradient, the gray scale being the most ideal.

Thermal asymmetries result from functional changes in the organism, therefore, a difference above 0.3° C. is suggestive of abnormality and above (GOODMAN, 1986) of 1° C. is a strong indication of dysfunctions (DIBENEDETO, 2002).

In the perspective of Ring and Ammer (2007), the infrared image can only produce reliable and valid results if the technique follows established standards, where the capture of the image must take place in a controlled environment.

Different authors disagree with the temperature of the environment, to perform the exam. Such a recommendation is directly related to the type of tissue submitted to the examination, with a temperature range of 18° C.-25° C. being observed (LAHIRI, 2012).

Infrared radiation can interact with the mass of surrounding gases, having several of their wavelengths absorbed and sent (atmospheric attenuation), by the presence of gases containing three or more atoms in the molecule and solid particles in suspension (VERATTI, 1992; NOGUE IRA, 2010).

The distance between the camera and the tissue under study are not relevant factors for the success of the exam. The ideal distance for image analysis of the abdomen and torso appeared to be around 2 meters, but greater or lesser distances did not lead to statistically significant variations in relation to the exported data (TOPALIDOU, 2016).

In 2000, Anbar suggested that small tumors are capable of producing notable changes in the infrared image, which could occur via nitric oxide vasodilation induced by ductal carcinoma in situ (DICS).

The growth of a tumor depends on neovascularization, and this successful recruitment of new blood vessels in a tumor (angiogenesis) depends on angiogenic growth factors produced by the tumor cells. The new vessels grow adjacent to the tumor and have no smooth muscle, making them refractory to the control by epinephrine. This maintains a more constant blood flow that increases the local temperature (SALHAB, 2005).

The regions, of the breast with cancer, produce thermal signals with changes in complexity when analyzed over time, where 90.90% of the correctness rate was reached (SILVA, 2015).

Thermometry is used in several cardiac surgeries because the infrared radiation emitted by the heart is directly proportional to its temperature, and this is directly proportional to the coronary flow (ROBICSEK, 1978). Thus, a high emission of heat by the myocardial tissue indicates an increase in blood flow, while a decreased emission indicates a hypoperfusion. The high cardiac blood flow and its considerable metabolic activity make the myocardium being an excellent organ for examination by infrared thermometry (BRIOSCHI, 2002).

In addition to the uses already described, other applications are targeted by the technique, such as the treatment and control of pain, vasculopathies, rheumatic diseases, neurology, surgery, ophthalmology, dermatology, burns, ulcers, dentistry, respiratory disorders, sport and physical rehabilitation.

Infrared emissions from human skin at 27° C. are within the wavelength range from 2 to 20 μm, peaking at around 10 μm. The wavelength range between 8-12 μm is called body infrared radiation (LIR), however, with the new generations of detectors, the NIR and MIR regions are also being used (LAHIRI, 2012).

Figure 1:
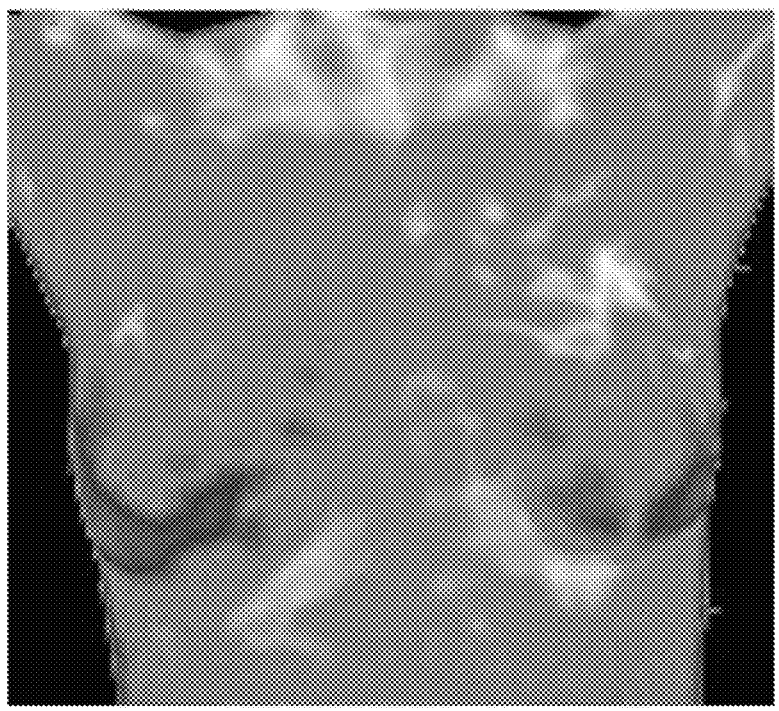
FIG. 1 shows the image of breast cancer (ductal carcinoma in situ) in two colors, in the MIR infrared region (SZU, 2003).
Figure 2:
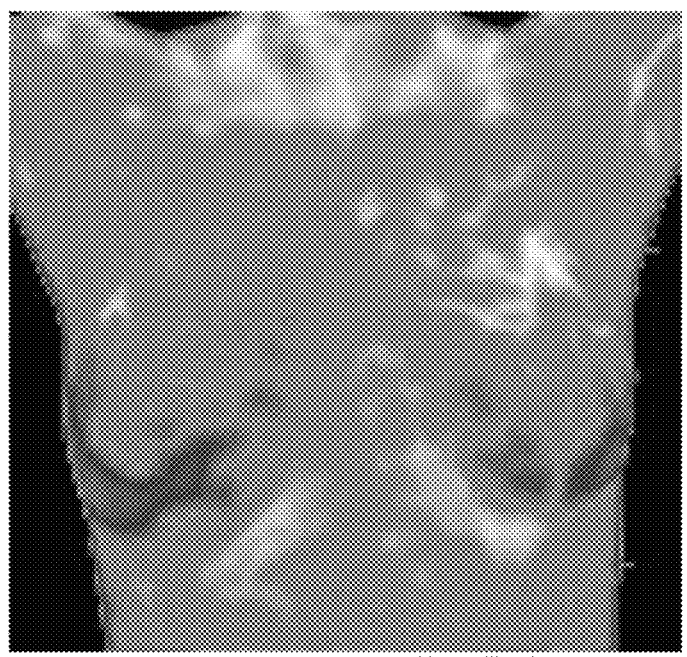
FIG. 2 shows the image of breast cancer (ductal carcinoma in situ) in two colors in the LIR infrared region (SZU, 2003).
Figure 3:
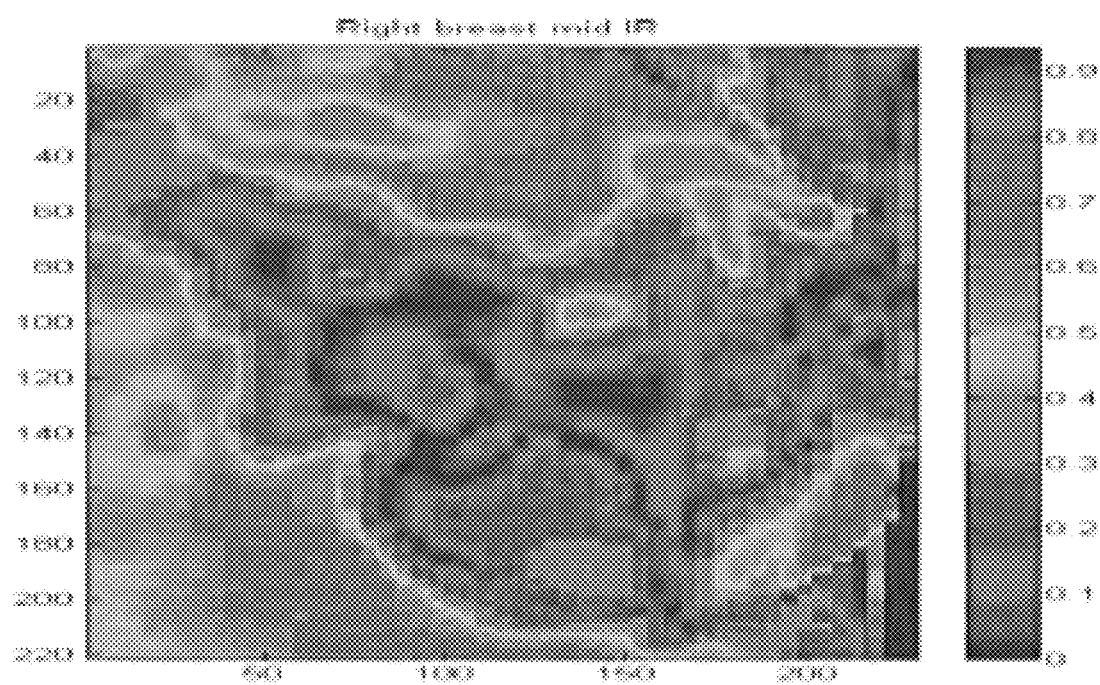
FIG. 3 shows the image of the right breast in the MIR range (left) (SZU, 2003).
Figure 4:
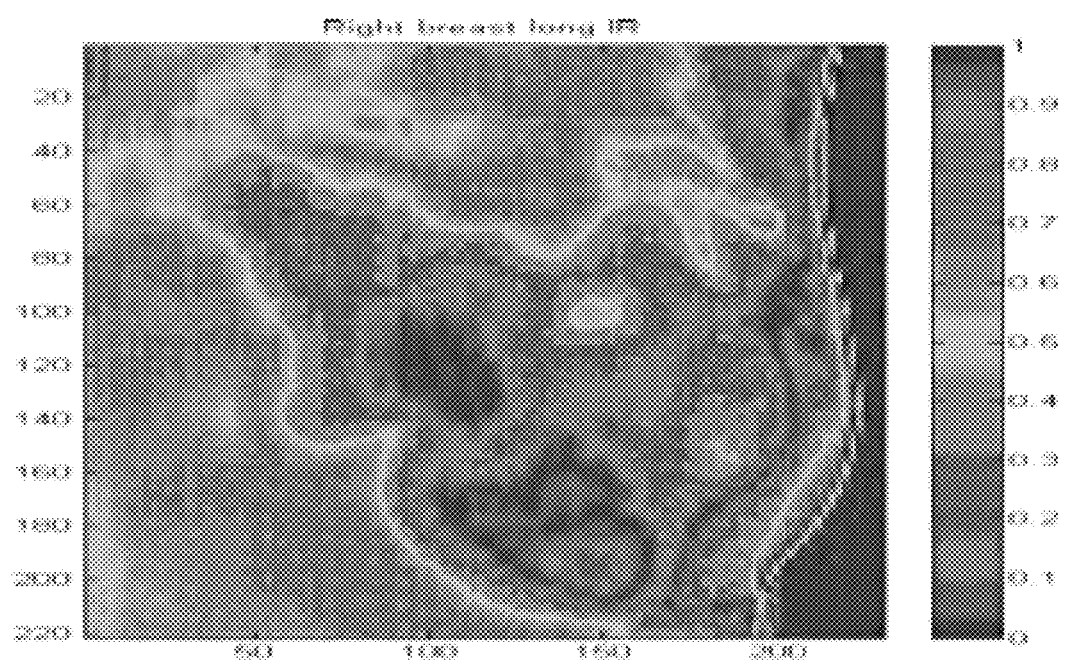
FIG. 4 shows the image of the right breast LIR (right) showing an enhancement in the delimitation (SZU, 2003).

During an experiment carried out in 2003 by Szu, as shown in FIGS. 3 and 4, it became evident that, depending on the infrared regions, some details may be lost when choosing one or the other infrared region.

Figure 5:
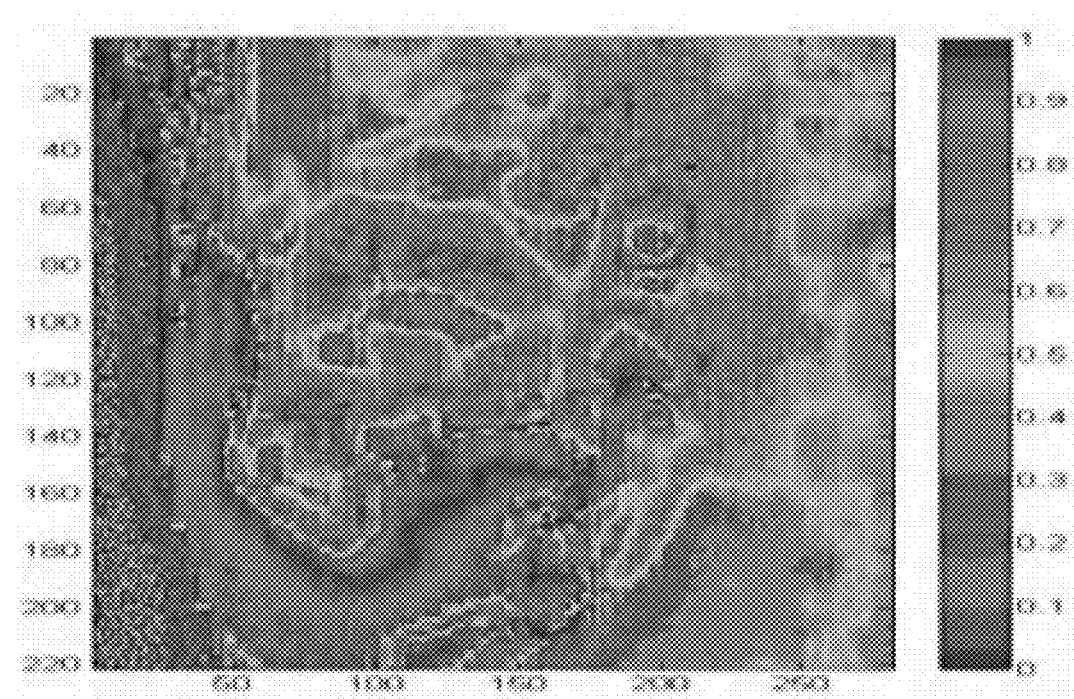
FIG. 5 shows the multicolored image of the breast before the application of the LCCN (language constraint neural network) algorithm (SZU, 2003).
Figure 6:
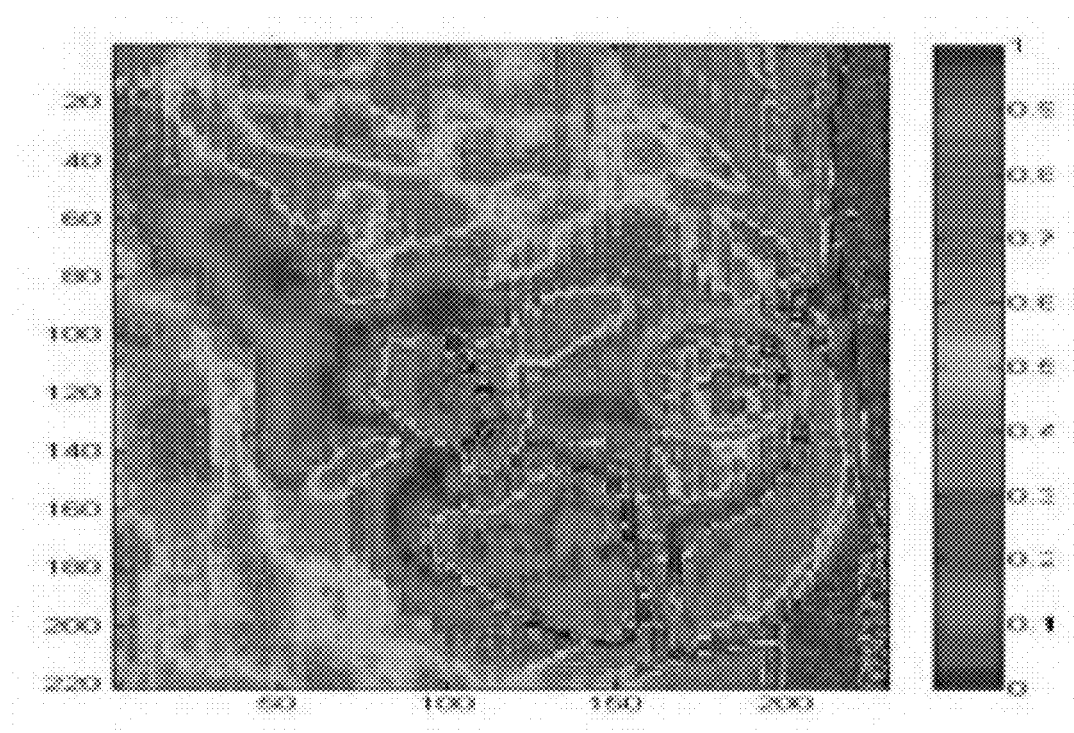
FIG. 6 shows the application of the LCCN algorithm in the multicolored image of the breast where it was evidenced the lesion, marked in pink (SZU, 2003).

In addition, FIGS. 5 and 6 show that using a multispectral algorithm LCCN (Lagrange Constraint Neural Network) in multicolored images, a hyper-radiant area is evidenced in the carcinoma lesion in situ, in the breast region, despite the limitation of the technique in 2003. These details can change the assessment of a patient's health situation and the treatment method that can be used.

During the experiment, it was reported that the infrared image with two colors can correctly register the asymmetries and provide a better diagnosis in breast cancer, and even compared the same image in the LIR and MIR regions, according to FIGS. 3 and 4.

Figure 7:
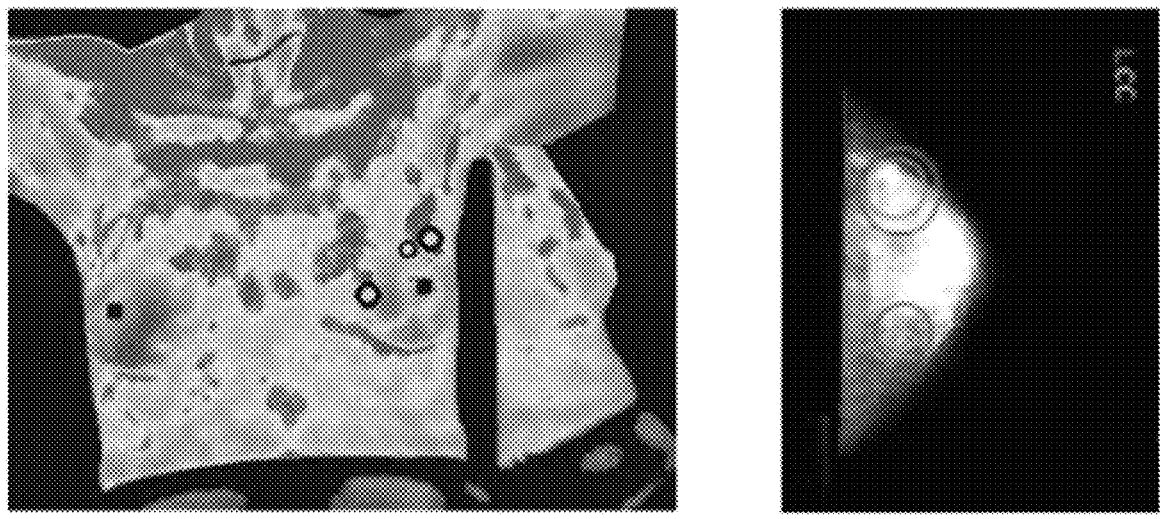
FIG. 7 shows an example of thermal asymmetry detected by a color palette.
Figure 8:
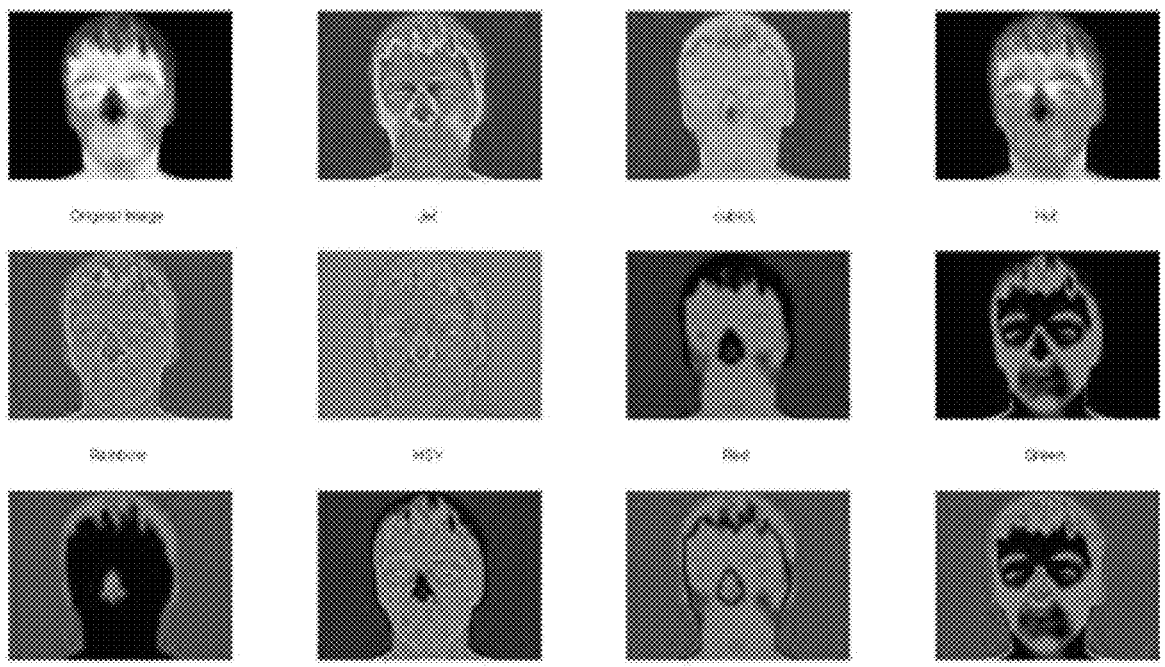
FIG. 8 shows the color pattern used in the industrial image and adapted for image tests.

Another important position was given by Arena in 2004, when he suggested the combination of modalities in a single display, where the data could be color-coded and layered, improving perception in a clear and concise image, according to FIG. 7.

If, on the one hand, the R/D algorithm and the color pattern of industrial software are the most used, on the other hand, the long infrared range (LIR) no longer receives information from the other ranges that also reflect the molecular movement, showing that the technique is effective, but is not using the proper technology.

Infrared emissions from human skin at 27° C. are within the wavelength range from 2 to 20 μm, with peak at around 10 μm, with the LIR being used more.

The method of processing thermometric video images of patients uses MIR and LIR infrared emissions for visualization the macro aspect and delimitation of the region of interest. The NIR is intended for the micro aspect (spectrum identification), after the previous delimitation of the MIR and LIR.

Processing of thermometric video images of a patient comprises the process of delimiting the area from which it is necessary to obtain information, generate a video thermogram and manipulate this video thermogram by adjusting the resolution.

Keeping in mind, about the particularities mentioned above as each human tissue has a particular emissivity, emitting heat in different ranges of the infrared region, the difference in the normal skin temperature on both sides of the human body, is around 0.2° C. Thermal asymmetries result from functional changes in the organism, therefore, a difference above 0.3° C. is suggestive of abnormality and above 1° C. is a strong indication of dysfunctions.

For industrial inspection it is justifiable to obtain information on all temperatures emitted by the object, since it tends to enter thermal equilibrium, but for humans only extreme temperatures are important, since we are homeothermic and maintain our constant internal temperature. The peripheral temperature can vary uniformly with the environment, but in a pathology, we have a temperature difference between pixels that can reach degrees. Hence the importance of the sensitivity of the equipment to be used and the capture of the temperatures that interest us according to the pathology to be studied.

The segmentation of the medical image is critical for the design of anatomical structures and other regions of interest. Color and texture are the two low-level features, and also the most important ones used for content-based retrieval of information in images and videos, and are often used to index and manage data.

In order to the construction of the palette to be appropriate to the pathology, it is necessary to know what is expected to be found since each disease has its own particularity. The ideal is the inspection of the area of interest and find the maximum and minimum temperature, building the color ranges of the palette from this parameter.

It is also important to use segmentation to cancel information from regions that do not interest us, facilitating the analysis of the image from where the region of interest is, as shown in FIG. 52.

In addition to segmentation, isotherms are demarcating resources, which can be used in regions of interest, facilitating the location of areas, as shown in FIGS. 53 to 56.

In every process of creating palettes, the number of colors, the positioning and the association of one or two isotherms can change more information than was understood in the state of the art. In all cases, the enhancement of the image, even without resources, shows that the infrared image can give more visual information, than temperature differences. In one embodiment, the color palettes are stored inside the system for processing thermometric video images of patients. In another embodiment, color palettes are acquired through a means of acquiring color palettes in the cloud.

In a second object, the present invention features a system for processing thermometric video images of patients comprising:
  a. means of acquisition of the video thermogram comprising at least one reading head; and
  b. means of manipulating of the video thermogram configured to receive the video thermogram generated by the means of acquisition.

In one embodiment, the means of acquisition comprises a reading head with technology in the infrared bands NIR, MIR and LIR associated with a camera for image fusion. In one embodiment, said camera is a CCD camera. Therefore, the system makes it possible to carry out a fusion between the real image, captured by the camera, and the image of the video thermogram, captured by the reading head.

In order to the image being analyzed in real time, in addition to the construction of the palettes, there must be an environment so that it can be improved. It is also necessary that there are tools that can be used to adapt it to the situation to be studied, making the technique reproducible. In one embodiment, the system for processing thermometric video images of patients comprises three modules that interact with each other for the manipulation of video thermograms, comprising the user module, the administrator module and the developer module.

Video thermogram is any image detected where the different temperatures of the analyzed region are evidenced.

The user module presents access profile controls. A user must be associated with at least one access profile, which determines the responsibility and/or level of access to the system's information, either as co-administrator of the information, or as a mere customer for the administration of his own information. In addition, the user module has a printing of reports, where such reports comprise a description of the procedure in text, images and/or videos that involve a previous registration of the client and his history.

The administrator module allows a wide use of the object's functionalities, support for software installation, report center, telemedicine and updates. In an additional embodiment, the administrator module has privileged access to all functions of the object for allowing support.

The developer module has the system controls itself and comprises administration by users with a high level of knowledge and responsibility. In an additional embodiment, the developer module keeps all the parameterization controls of the other modules, either databases, color palettes, isotherms, graphs, statistical data, with permission to edit the source code and generate the object.

In the system for processing thermometric video images of patients, palette editing is a module that allows the editing of new palettes. In one embodiment, it is a function to be used outside of real time, and that collaborates updating the software.

In one embodiment, the color palette edition allows the reading of palettes not resident in the system to generate the new image pattern, as exemplified by FIGS. 40 to 50, so that it has an intuitive presentation, with practical controls associated facilitating tools, such as function keys for shortcuts while working.

In an additional embodiment, the editing module resembles a big wheel, as shown in FIGS. 59 and 60, showing the image of the palettes residing in the software, in video and/or static image by scrolling the mouse. Once the best image is selected, two clicks with the mouse on the chosen option transfer this image to the main screen, which can be edited using segmentation and isotherms.

In one embodiment, when choosing the best gradient background option, the improvement is done by the "Merlin bar" tool, as shown in FIG. 60. Once activated, this bar has the top and bottom buttons in addition to a link bar. After grouping, the palette can be moved by the mouse to the desired position on the temperature bar. The grouped range refers to a gradient of predefined colors, which becomes mobile, over a uniform gradient color and/or with a pre-established pattern. In addition, the isotherms (solid and isolated colors) also move in the vertical temperature bar in search of temperature changes from 0.1 to 5° C. searching for asymmetries. For example, the choice of the 0.3° C. isotherm seeks discrepant areas of 0.3° C. in relation to its position in the vertical temperature bar, pointing out areas to be investigated. FIG. 60 shows an embodiment of the use of a system functionality for image enhancement by the "Merlin bar" tool.

In the fusion of technologies, the NIR can capture the image of the discrepant area creating a spectrum that can identify the molecular structure and compare it to the spectra bank already registered, generating a real-time diagnosis of the area to be investigated or not.

In one embodiment, the system for processing thermometric video images of patients comprises image conversion to the medical digital image communication system (DICOM), where the information becomes a file to communicate with other software and query. As radiometric images, these can be edited again with the evolution of technology.

In an additional embodiment, the system for processing thermometric video images of patients comprises 3D fusion between computed tomography images and/or nuclear magnetic resonance with thermal images, in order to work efficiently in terms of reconstruction and processing speed, as exemplified by FIG. 64.

Example 1

The examples shown here are intended only to exemplify one of the several ways of carrying out the invention, however without limiting the scope of it.

The means of acquisition/capture of the image is realized by the reading head with technology in the infrared ranges: NIR, MIR and LIR, associated with a CCD camera for the fusion of images with an associated exhaustion and cooling unit.

With a scientific thermal camera and ResearchIR software, an industrial-standard, multicolored output image was generated, which can be considered an excellent technology today, despite being far away of the ideal.

Since the evidences show that, in pathological situations, the metabolic intensity increases and generates heat (as a result of chemical reactions and molecular movement), it was evident that the occurrences were happening, but they were not being visualized.

The first step was the construction of palettes from the captured images, where the palettes should be built by tissues and organs.

The construction of the palettes was made from rats and rabbits that underwent some experiment at the Animal Experimentation Unit (UEA-RJ). Because they have a high metabolic intensity, it was possible to create a color pattern that made it possible to evidence the outline of anatomical structures shown in FIGS. 28 and 33.

Subsequently, we tried to see if it would be possible to see the flow of blood in the heart during open chest surgery on a rabbit. The blood flow, shown in FIG. 11 in blue, was evident when entering the caudal vena cava towards the right atrium and right ventricle.

Several palettes were built for obtaining this image, in order to choose the option that showed the best clarity on video. FIG. 12 shows several color palettes built.

When blood flow is visualized, the lymphatic flow with the knowledge that the identification of lymphatic tissue, in the state of the art, is a problem even for the most trained surgeon.

In this way, in the routine of healthcare at the UEA, an inspection was carried out on the dog during an open chest surgery to correct a chylothorax, as shown in FIGS. 34 to 39. Chylothorax is a debilitating condition where there is rupture of the thoracic duct and consequent leakage of the chyle in the pleural space. The chyle is a milky lymphatic liquid resulting from the absorption of fats from the digestive process that has a high concentration of chylomicrons, and lipoproteins such as triglycerides, phospholipids and cholesterol (ALLMAN, 2010). The identification of the thoracic duct is essential for the correction of the overflow of the chyle.

In every process of creating palettes, it is possible to realize that the number of colors, the positioning and the association of one or two isotherms can give more information than being used in the state of the art. In all cases, it is possible to improve the image, even without recourse, showing that the infrared image can give more visual information, in addition to temperature differences.

Example 2

A different case for using the method for processing thermometric video images is exemplified in FIG. 65.a and 65.b, previously explained in FIGS. 13 to 16. Since the images are radiometric, it is possible to re-analyze all the images captured at the beginning of the experiment, reconstructing the new pattern as the processing logic is repeated. In this way, it is possible to visualize textures that could not be seen before.

Example 3

In another case, it was possible to identify areas similar to the known tumor area, but without visible or palpable changes, being the object of a biopsy that resulted in a neoplastic embolus, according to FIGS. 17 to 19.

In addition to the ease of visualization and the definition of lesions, the temperature measurement is an important indicator of dysfunction. It is also possible to identify the extent of the tumor and metastases at a distance in another palette, shown in FIGS. 21 to 23.

It is important to say that the technique can also be applied to evaluate pulmonary ventilation, according to the respiratory movements that appear in FIGS. 28 to 30.

In mesentery, it allows to check vascularity and dysfunctional areas. In this case, a palette was built to check a fecaloma, where the intestinal loop is distended, shown in FIGS. 31 to 33.

Example 4

In rats, the growth of melanoma (tumor) in the ear was induced, making it possible to identify which animals developed tumors, and the area of tumor coverage, regardless of visible signs, as shown in FIGS. 26 and 27.

Example 5

MART Station (1)

In order to exemplifying the system for processing thermometric video images of patients, referred to in this example as a metabolic activity in real-time station (MART) (1), FIG. 68 shows an embodiment of the MART station (1) in five different uses.

The MART station (1) is a computerized editing station, coupled to an image generator, which captures the static and/or dynamic digital image, free of radiation, emitted by the body through infrared sensors, being able to record videos and transform them into data.

Thermometry video in the detection of metabolic changes can assist the decision-making process, since the MART station (1) uses a new image pattern, developed by affection, organ or tissue, is effective in recording occurrences, which in spite of the fact that not visible to the naked eye, are present.

MART station (1) for use in the operating room (1.1) comprises:
  a. delimitation of tumor coverage and margins;
  b. identification of tumor vascularization;
  c. presumptive biopsies of metastasis at a distance;
  d. identification of vascular abnormalities, including lymphatic ones;
  e. identification of areas of ischemia.

MART station (1) for use in radiology (1.2) comprises:
  a. identification of vascular abnormalities of the breast;
  b. identification of thermal asymmetry indicative of dysfunction;
  c. delimitation of tumor coverage and margins;
  d. identification of areas of ischemia.

MART Station (1) for use in dermatology (1.3) comprises:
  a. identification of thermal asymmetry indicative of dysfunction;
  b. delimitation of tumor coverage and margins;
  c. identification of vascular abnormalities or tumor irrigation;
  d. Identification of stem-cell niches.

MART station (1) for use in cardiology (1.4) comprises identification of ischemia during effort testing.

MART station (1) for laboratory use (1.5) (before visible changes) comprises:
  a. identification of cellular disposition in the culture medium;
  b. identification of cell growth, competition or death
  c. visualization of cellular energetic behavior.

Use of reading heads with technology in the infrared ranges: NIR, MIR and LIR, associated with a CCD camera for image fusion.

MIR and LIR are intended for viewing the macro aspect and delimiting the region of interest. NIR is intended for the micro aspect (identification of the sample spectrum), after the previous delimitation of MIR and LIR. With this, the system uses the "Spectral" tool that comprises capturing the NIR image to form the sample spectrum in an image. FIG. 69 shows an example of a spectrum obtained through this tool.

Infrared vibrational spectroscopy can extract information about the structure and composition of various biological materials from molecular movement (LEE, 2009). Spectroscopy in the NIR region can be an excellent technology association. With each type of bond it has its own natural frequency of vibration, and since two identical types of bonds in two different compounds are in two slightly different environments, absorption patterns in the infrared, or infrared spectrum, in two molecules of different structures are never exactly identical. Although the frequencies absorbed in the two cases may be the same, the infrared spectra (the absorption patterns) of two different molecules will never be identical. Thus, the infrared spectrum can serve molecules in the same way that fingerprints do for humans, as shown in FIG. 66. Two types of infrared spectrometers are widely used in chemical laboratories: dispersive and Fourier transform (FT) instruments. However, FT infrared spectrometers produce the spectrum much more quickly than dispersive instruments (PAIVA, 2010).

Presumptive areas can be analyzed using specific parameters obtained from Fourier transform infrared spectra, making it a fast and reagent-free method that can distinguish premalignant and malignant cells and tissues from their normal state (SAHU, 2005). FIG. 67 shows an embodiment of that spectrum.

Those skilled in the art will appreciate the knowledge presented here and will be able to reproduce the invention in the modalities presented and in other variants and alternatives, covered by the scope of the following claims.

The invention claimed is:

1. A method for processing thermometric video images of patients comprising the steps of:
   a) delimiting a region of interest and recording of anomalies not visible to the naked eye, through the emission of electromagnetic waves MIR and LIR;
   b) taking thermometry video of the region of interest through the emission of electromagnetic waves MIR and LIR;
   c) identifying anomalies not visible to the naked eye for spectral analysis of the sample through the emission of NIR electromagnetic waves;
   d) adjusting the resolution of the generated video thermogram;
   e) detecting discrepancies of temperatures in the region of interest, after the step of taking thermometry video; and
   f) constructing color ranges of a color palette on a uniform gradient background capable of moving over a maximum temperature bar and minimal forming a desired thermometric video image,
   wherein the color palette comprises a bar tool that groups and moves a predetermined temperature range, represented by solid colors, over the uniform gradient background.

2. The method for processing thermometric video images according to claim 1, wherein the color palette comprises a combination of colors, positioning and movement associated with one or more isotherms.

3. The method for processing thermometric video images according to claim 2, wherein the selected isotherms are grouped at predetermined intervals, on the maximum and minimum temperature bar, in which the isotherms can be moved to find the desired thermometric video image.

4. The method for processing thermometric video images according to claim 1, further comprising a step of application of the color palette in the generated video thermogram.

5. A system for processing thermometric video images of patients, comprising:
   a) means of acquisition of a video thermogram comprising at least one reading head; and
   b) manipulating the video thermogram configured to receive the video thermogram generated by the means of acquisition,
   wherein the means of manipulating the video thermogram comprises a uniform gradient base, forming a maximum and minimum temperature bar of the thermometric video image; and a color palette, built with a range of colors, that moves over that temperature bar to find the desired thermometric video image, and
   wherein the color palette comprises additionally a parallel bar of isotherms, in which a predetermined temperature range, represented by solid colors, is selected to be moved over the temperature bar finding similar temperature areas.

6. The system for processing thermometric video images according to claim 5, wherein the means of acquisition comprises a reading head in the infrared bands NIR, MIR and LIR associated with a camera for image fusion.

7. The system for processing thermometric video images according to claim 6, wherein the acquisition in the NIR infrared range generates a sample spectrum in the thermometric video image.

8. The system for processing thermometric video images according to claim 5, wherein the means of manipulating the video thermogram comprises a simultaneous visualization tool of the existing color palettes, represented by superimposed mini images, in which the overlays of mini images are highlighted when selected for manipulating the thermometric video image.

9. A method for processing thermometric video images of patients comprising the steps of:
   a) delimiting a region of interest and recording of anomalies not visible to the naked eye, through the emission of electromagnetic waves MIR and LIR;
   b) taking thermometry video of the region of interest through the emission of electromagnetic waves MIR and LIR;
   c) identifying anomalies not visible to the naked eye for spectral analysis of the sample through the emission of NIR electromagnetic waves;
   d) adjusting the resolution of the generated video thermogram;
   e) detecting discrepancies of temperatures in the region of interest, after the step of taking thermometry video; and
   f) constructing color ranges of a color palette on a uniform gradient background capable of moving over a maximum temperature bar and minimal forming a desired thermometric video image,
   wherein the color palette comprises a combination of colors, positioning and movement associated with one or more isotherms, and
   wherein the selected isotherms are grouped at predetermined intervals, on the maximum and minimum temperature bar, in which the isotherms can be moved to find the desired thermometric video image.

* * * * *